United States Patent [19]

Watson et al.

[11] Patent Number: 4,666,510
[45] Date of Patent: May 19, 1987

[54] CYCLOHEXENONE DERIVATIVES AND THEIR HERBICIDAL USE.

[75] Inventors: Keith G. Watson, Box Hill North; Lynette A. Garson, Parkville; Graham J. Bird, North Melbourne; Lindsay E. Cross, Maribyrnong; Graeme J. Farquharson, Reservoir, all of Australia

[73] Assignee: ICI Australia Limited, Melbourne, Australia

[21] Appl. No.: 460,854

[22] Filed: Jan. 25, 1983

[30] Foreign Application Priority Data

Jan. 29, 1982 [AU] Australia ............................... PF2489
Jul. 14, 1982 [AU] Australia ............................... PF4865

[51] Int. Cl.⁴ ..................... A01N 31/08; A01N 33/08; C07C 131/00; C07C 83/00
[52] U.S. Cl. ..................... 71/103; 558/412; 560/12; 560/13; 560/18; 560/21; 560/35; 560/64; 560/65; 560/73; 560/251; 560/252; 564/85; 564/86; 564/87; 564/179; 564/220; 564/256; 564/300; 71/98; 71/105; 71/107; 71/111; 71/121
[58] Field of Search ..................... 564/256, 85, 86, 87, 564/179, 220; 71/12, 98, 103, 105, 106, 107, 111, 121; 260/465 D, 465 E; 560/12, 13, 18, 21, 35, 64, 65, 73, 107, 251, 252; 558/412

[56] References Cited

U.S. PATENT DOCUMENTS 3,950,420  4/1976  Sawaki et al. ..................... 564/256
3,989,737  11/1976  Sawaki et al. ..................... 71/98

OTHER PUBLICATIONS

Conant, James Bryant et al. *The Chemistry of Organic Compounds,* 4th Ed. (1954) The MacMillan Co., Publ. at p. 335.
Iwataki, I. et al., *Advances in Pesticide Science*—Part 2 (1979) Permagon Press, Publ., pp. 234–243.

*Primary Examiner*—Natalie Trousof

*Assistant Examiner*—L. Hendriksen
*Attorney, Agent, or Firm*—Cushman, Darby & Cushman

[57] ABSTRACT

The invention concerns novel compounds of the formula I

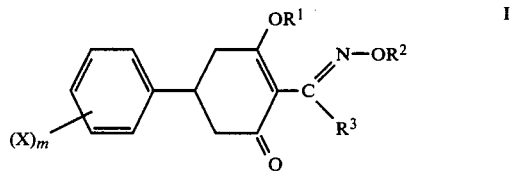

wherein:
X is selected from halogen, nitro, cyano, alkyl, substituted alkyl, hydroxy, alkoxy, substituted alkoxy, alkenyl, alkynyl, alkenyloxy, alkynyloxy, acyloxy, alkoxycarbonyl, alkylthio, alkylsulfinyl, alkylsulfonyl, sulfamoyl, substituted sulfamoyl, amino, substituted amino, and the groups formyl and alkanoyl and the oxime, imine and Schiff base derivatives thereof;
$R^1$ is selected from hydrogen, alkyl, alkenyl, alkynyl, substituted alkyl, alkylsulfonyl, arylsulfonyl, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl;
m is an integer chosen from 3 to 5.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

15 Claims, No Drawings

CYCLOHEXENONE DERIVATIVES AND THEIR HERBICIDAL USE.

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium(methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as U.K. Pat. No. 1 461 170 and U.S. Pat. No. 3 950 420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No AU-A1-35,314/78 and its equivalents.

It has now been found that a new group of cyclohexane-1,3-dione derivatives which have a 5-phenyl substituent which is in turn substituted with three or more substituents exhibit particularly useful herbicidal activity and plant growth regulating activity.

Accordingly the invention provides a compound of formula I:

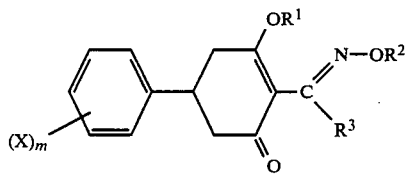

wherein:

X, which may be the same or different, are selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^8R^9$ wherein $R^8$ and $R^9$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof; and at least one of X is not selected from the group consisting of halogen, $C_1$ to $C_6$ alkyl and $C_1$ to $C_6$ alkoxy;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and m is an integer chosen from 3 to 5.

When in the compound of formula I X is chosen from the groups formyl and $C_2$ to $C_6$ alkanoyl and the oxime, imine and Schiff base derivatives thereof, the nature of the oxime, imine and Schiff base derivatives is not narrowly critical. Although not intending to be bound by theory, it is believed that in the plant the (substituted) imine group may be removed to give the corresponding compound of formula I in which X is formyl or $C_2$ to $C_6$ alkanoyl. Suitable values for the groups formyl and $C_2$ to $C_6$ alkanoyl and the oxime, imine and Schiff base derivatives thereof include groups of the formula $—C(R^{10})=NR^{11}$ wherein $R^{10}$ is chosen from hydrogen and $C_1$ to $C_5$ alkyl, and $R^{11}$ is chosen from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is chosen from acyl the nature of the acyl group is not narrowly critical. Although not intending to be bound by theory, it is believed that when $R^1$ is acyl the acyl group is removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation is removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^4R^5R^6R^7N^\oplus$ wherein $R^4$, $R^5$, $R^6$ and $R^7$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of three tautomeric forms as shown below:

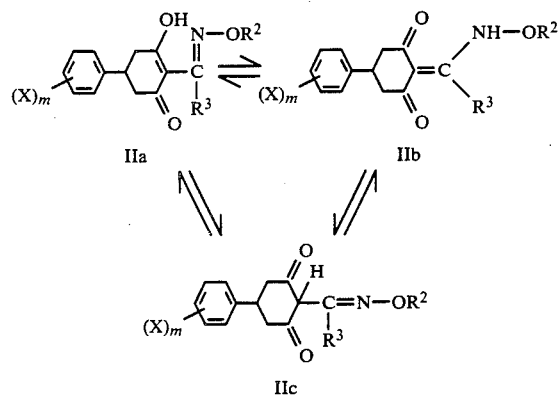

IIa    IIb

IIc

Suitable X, which may be the same or different, include: halogen; nitro; cyano; $C_1$ to $C_6$ alkyl; $C_1$ to $C_6$ alkyl substituted with a substituent selected from the group consisting of halogen; nitro and $C_1$ to $C_6$ alkoxy; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkanoyloxy; amino; $C_1$ to $C_6$ alkylamino; di($C_1$ to $C_6$ alkyl)amino; $C_1$ to $C_6$ alkanoylamino; benzoylamino; formyl; $C_2$ to $C_6$ alkanoyl; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; and N,N-di($C_1$ to $C_6$ alkyl)sulfamoyl; at least two of X are methyl and at least one of X is not selected from the group consisting of halogen, $C_1$ to $C_6$ alkyl and $C_1$ to $C_6$ alkoxy.

Suitable $R^1$ include hydrogen, benzoyl, substituted benzoyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl, and the group M wherein M is an alkali metal ion.

Suitable $R^2$ include $C_1$ to $C_6$ alkyl, $C_2$ to $C_6$ alkenyl, $C_2$ to $C_6$ alkynyl, benzyl and substituted benzyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkoxy.

Suitable $R^3$ include $C_1$ to $C_6$ alkyl.

Preferred X include: halogen; nitro; cyano; hydroxy; $C_1$ to $C_4$ alkyl; $C_1$ to $C_4$ alkoxy; $C_2$ to $C_4$ alkenyloxy; $C_1$ to $C_4$ alkylthio; $C_1$ to $C_4$ alkylsulfinyl; $C_1$ to $C_4$ alkylsulfonyl; formyl, $C_2$ to $C_6$ alkanoyl and the oxime O-$C_1$ to $C_4$ alkyl ethers thereof; $C_2$ to $C_6$ alkanoyloxy; benzyloxy; sulfamoyl; N,N-di($C_1$ to $C_4$ alkyl)sulfamoyl; $C_1$ to $C_4$ alkyl substituted with a substituent selected from the group consisting of nitro, hydroxy, $C_1$ to $C_4$ alkoxy and $C_1$ to $C_4$ alkylthio; $C_1$ to $C_4$ alkoxy substituted with one or more substituents selected from halogen; the group $NR^8R^9$ wherein $R^8$ and $R^9$ are independently selected from hydrogen and $C_2$ to $C_4$ alkanoyl.

Preferred $R^1$ include: hydrogen; $C_2$ to $C_6$ alkanoyl such as acetyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy, benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or organic cation selected from the cations of the alkali metals such as lithium, potassium and sodium, the cations of the alkaline earth metals such as magnesium, calcium and barium, the cations of the transition metals such as manganese, copper, zinc, iron, nickel, cobalt and silver, the ammonium ion and the tri- and tetra-(alkyl)ammonium ions wherein alkyl is selected from $C_1$ to $C_6$ alkyl and $C_1$ to $C_6$ hydroxyalkyl.

Preferred $R^2$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; and $C_2$ to $C_6$ haloalkynyl.

Preferred $R^3$ include $C_1$ to $C_6$ alkyl.

More preferred compounds of the invention include those compounds of formula I in which the benzene ring is substituted in the 2- and 6-positions. That is compounds of formula

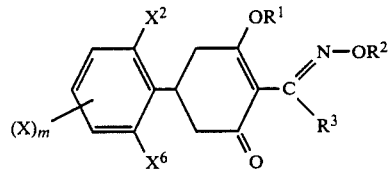

wherein:

X, $X^2$ and $X^6$ are independently selected from the group consisting of halogen, nitro, cyano, hydroxy, amino, methyl, ethyl, methoxy, methylmercapto, n-butylmercapto, nitromethyl, hydroxymethyl, methoxymethyl, ethoxymethyl, n-butylthiomethyl, difluoromethoxy, allyloxy, benzyloxy, methylsulfinyl, methylsulfonyl, formyl, formyl oxime O-ethyl ether, acetyl, butyryl, propionyl, acetyloxy, sulfamoyl, N,N-dimethylsulfamoyl and acetylamino, and at least one of X, $X^2$ and $X^6$ is not selected from the group consisting of halogen, methyl, ethyl and methoxy; $R^1$ is selected from the group consisting of hydrogen, acetyl, benzoyl, nitrobenzoyl, methylbenzenesulfonyl and the cations of the alkali metals;

$R^2$ is selected from the group consisting of $C_1$ to $C_3$ alkyl, 2-haloethyl, allyl and 2-haloallyl;

$R^3$ is selected from the group consisting of $C_1$ to $C_3$ alkyl; and m is an integer selected from 1 to 3.

Preferably the substituents in the 2- and 6-positions of the benzene ring are independently selected from halogen, methyl, methoxy and methylmercapto.

Even more preferred compounds of the invention include those compounds of formula I in which the benzene ring is substituted in the 2-, 3- and 6-positions and wherein the substituents in the 2- and 6-positions are methyl. That is, compounds of formula

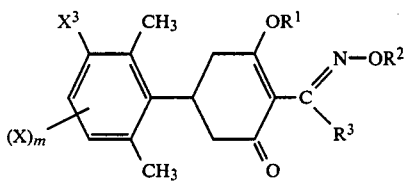

wherein:

X and $X^3$, which may be the same or different, are selected from the group consisting of halogen, methyl, ethyl, methoxy, methylmercapto, nitromethyl, hydroxymethyl, methoxymethyl, ethoxymethyl, methylsulfinyl, methylsulfonyl, acetyl, propionyl, sulfamoyl and N,N-di(methyl)sulfamoyl, and at least one of X is not selected from the group consisting of halogen, methyl, ethyl and methoxy;

$R^1$ is selected from the group consisting of hydrogen, acetyl, benzoyl, nitrobenzoyl, methylbenzenesulfonyl and the cations of the alkali metals;

$R^2$ is selected from the group consisting of $C_1$ to $C_3$ alkyl, 2-haloethyl, allyl and 2-haloallyl;

$R^3$ is selected from the group consisting of $C_1$ to $C_3$ alkyl; and m is 0 or an integer selected from 1 and 2.

Further preferred compounds of the invention include those compounds of formula

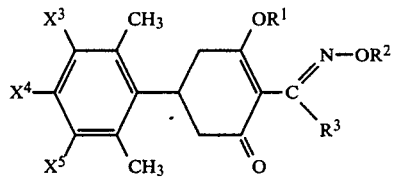

wherein:

$X^3$ is selected from the group consisting of methylmercapto, nitromethyl, methoxymethyl, ethoxymethyl, methylsulfinyl, methylsulfonyl, acetyl, propionyl, sulfamoyl and N,N-dimethylsulfamoyl;

$X^4$ is selected from hydrogen and methyl;

$X^5$ is selected from hydrogen, methyl and ethyl;

$R^1$ is selected from hydrogen, sodium and potassium;

$R^2$ is selected from ethyl and allyl; and $R^3$ is selected from ethyl and n-propyl.

Specific examples of the compounds of the invention include those compounds detailed in Table 1 below.

TABLE 1

| Compound No. | $(X)_m$ | $R^1$ | $R^2$ | $R^3$ |
|---|---|---|---|---|
| 1 | 2,4,6-$(CH_3)_3$—3-$NO_2$ | H | $C_2H_5$ | $C_2H_5$ |
| 2 | 2,4,6-$(CH_3)_3$—3,5-$(NO_2)_2$ | H | $C_2H_5$ | $C_2H_5$ |
| 3 | 4-$CH_3$—3,5-$(NO_2)_2$ | H | $C_2H_5$ | $C_2H_5$ |
| 4 | 2,4-$(CH_3)_2$—6-$CH_3O$—3,5-$(NO_2)_2$ | H | $C_2H_5$ | $C_2H_5$ |
| 5 | 2,6-$(CH_3)_2$—3-$SO_2N(CH_3)_2$ | H | $C_2H_5$ | $C_2H_5$ |
| 6 | 2,4,6-$(CH_3)_3$—3-$NO_2$ | H | $C_2H_5$ | n-$C_3H_7$ |
| 7 | 2,4,6-$(CH_3)_3$—3-$NO_2$ | H | $CH_2CH=CH_2$ | n-$C_3H_7$ |
| 8 | 2,4,6-$(CH_3)_3$—3-$NH_2$ | H | $C_2H_5$ | n-$C_3H_7$ |
| 9 | 2,4,6-$(CH_3)_3$—3-$SOCH_3$ | H | $C_2H_5$ | $C_2H_5$ |
| 10 | 2,4,6-$(CH_3)_3$—3-$SO_2CH_3$ | H | $C_2H_5$ | $C_2H_5$ |
| 11 | 2,4,6-$(CH_3)_3$—3-$SO_2N(CH_3)_2$ | H | $C_2H_5$ | $C_2H_5$ |
| 12 | 2,4,6-$(CH_3)_3$—3-$SO_2NH_2$ | H | $C_2H_5$ | $C_2H_5$ |
| 13 | 2,4,6-$(CH_3)_3$—3-$COCH_3$ | H | $C_2H_5$ | $C_2H_5$ |
| 14 | 2,4,6-$(CH_3)_3$—3-$COCH_2CH_2CH_3$ | H | $C_2H_5$ | n-$C_3H_7$ |
| 15 | 2,4,6-$(CH_3)_3$—3-$CH=NOC_2H_5$ | H | $C_2H_5$ | n-$C_3H_7$ |
| 16 | 2,4,6-$(CH_3)_3$—3-$CH_3O$—5-$NO_2$ | H | $C_2H_5$ | $C_2H_5$ |
| 17 | 2,4,6-$(CH_3)_3$—3-Br—5-$NO_2$ | H | $C_2H_5$ | $C_2H_5$ |
| 18 | 2,5,6-$(CH_3)_3$—3-$O_2NCH_2$ | H | $C_2H_5$ | $C_2H_5$ |
| 19 | 3,4,5-$(CH_3)_3$—2,6-$(NO_2)_2$ | H | $C_2H_5$ | $C_2H_5$ |
| 20 | 2,3,4,6-$(CH_3)_4$—5-$NO_2$ | H | $C_2H_5$ | $C_2H_5$ |
| 21 | 4-HO—3,5-$(NO_2)_2$ | H | $C_2H_5$ | $C_2H_5$ |
| 22 | 2,4,6-$(CH_3)_3$—3-$COCH_3$—5-$C_2H_5$ | H | $C_2H_5$ | $C_2H_5$ |
| 23 | 2,6-$(CH_3)_2$—3-$NO_2$ | H | $C_2H_5$ | $C_2H_5$ |
| 24 | 2,3,5,6-$(CH_3)_4$—4-$COCH_3$ | H | $C_2H_5$ | $C_2H_5$ |
| 25 | 2,4,6-$(CH_3)_3$—3-$NHCOCH_3$ | H | $C_2H_5$ | $C_2H_5$ |
| 26 | 2,4,6-$(CH_3)_3$—3-CN | H | $C_2H_5$ | $C_2H_5$ |
| 27 | 2,3,4,6-$(CH_3)_4$—5-$COCH_3$ | H | $C_2H_5$ | $C_2H_5$ |
| 28 | 2,4-$(CH_3)_2$—3-Cl—6-$OCF_2H$ | H | $C_2H_5$ | $C_2H_5$ |
| 29 | 2,3,4,5-$(CH_3)_4$—6-$SCH_3$ | H | $C_2H_5$ | $C_2H_5$ |
| 30 | 2,3,5,6-$(CH_3)_4$—4-$SCH_3$ | H | $C_2H_5$ | $C_2H_5$ |
| 31 | 2,6-$(CH_3)_2$—4-OH | H | $C_2H_5$ | $C_2H_5$ |
| 32 | 2,3,4,5-$(CH_3)_4$—6-$SCH_3$ | H | $C_2H_5$ | n-$C_3H_7$ |
| 33 | 2,3,5,6-$(CH_3)_4$—4-$SCH_3$ | H | $C_2H_5$ | n-$C_3H_7$ |
| 34 | 2,6-$(CH_3)_2$—4-$O_2CCH_3$ | H | $C_2H_5$ | $C_2H_5$ |
| 35 | 2,4,6-$(CH_3)_3$—3-$COC_2H_5$ | H | $C_2H_5$ | $C_2H_5$ |
| 36 | 2,3,5,6-$(CH_3)_4$—4-OH | H | $C_2H_5$ | n-$C_3H_7$ |
| 37 | 2,4-$(CH_3)_2$—6-OH | H | $C_2H_5$ | n-$C_3H_7$ |
| 38 | 2,3,4,6-$(CH_3)_4$—5-$CH_2OCH_3$ | H | $C_2H_5$ | n-$C_3H_7$ |

TABLE 1-continued

Structure I:

$$\text{(X)}_m\text{-phenyl-cyclohexenone with } OR^1, =N-OR^2, R^3, =O \text{ substituents}$$

| Compound No. | $(X)_m$ | $R^1$ | $R^2$ | $R^3$ |
|---|---|---|---|---|
| 39 | 2,3,5,6-$(CH_3)_4$—4-$SC_4H_9$—n | H | $C_2H_5$ | n-$C_3H_7$ |
| 40 | 2,4,6-$(CH_3)_3$—3-$CH_2OCH_3$ | H | $C_2H_5$ | n-$C_3H_7$ |
| 41 | 2,4,6-$(CH_3)_3$—3-$CH_2OC_2H_5$ | H | $C_2H_5$ | n-$C_3H_7$ |
| 42 | 2,4-$(CH_3)_2$—6-$OCF_2H$ | H | $C_2H_5$ | n-$C_3H_7$ |
| 43 | 2,4,6-$(CH_3)_3$—3-$COCH_3$ | H | $C_2H_5$ | n-$C_3H_7$ |
| 44 | 2,3,4,5-$(CH_3)_4$—6-$SCH_3$ | $Na^\oplus$ | $C_2H_5$ | n-$C_3H_7$ |
| 45 | 2,3,4,5-$(CH_3)_4$—6-$SCH_3$ | H | $CH_2CBr=CH_2$ | n-$C_3H_7$ |
| 46 | 2,3,4,5-$(CH_3)_4$—6-$SCH_3$ | ½ Cu(2+) | $C_2H_5$ | n-$C_3H_7$ |
| 47 | 2,3,4,5-$(CH_3)_4$—6-$SCH_3$ | a | $C_2H_5$ | n-$C_3H_7$ |
| 48 | 2,3,5,6-$(CH_3)_4$—4-$OCH_2$—$C_6H_5$ | H | $C_2H_5$ | n-$C_3H_7$ |
| 49 | 2,6-$(CH_3)_2$—4-$OCH_2C_6H_5$ | H | $C_2H_5$ | $C_2H_5$ |
| 50 | 2,4-$(CH_3)_2$—6-$OCH_2C_6H_5$ | H | $C_2H_5$ | $C_2H_5$ |
| 51 | 2,4,6-$(CH_3)_3$—3-$CH_2OH$ | H | $C_2H_5$ | n-$C_3H_7$ |
| 52 | 2,3,5,6-$(CH_3)_4$—4-$OCH_2CH=CH_2$ | H | $C_2H_5$ | n-$C_3H_7$ |
| 53 | 2,3,4,5-$(CH_3)_4$—6-$SCH_3$ | H | $CH_2CH_2F$ | n-$C_3H_7$ |
| 54 | 2,4,6-$(CH_3)_3$—3-$COCH_3$ | $Na^\oplus$ | $C_2H_5$ | n-$C_3H_7$ |
| 55 | 2,4,6-$(CH_3)_3$—3-$COCH_3$ | b | $C_2H_5$ | n-$C_3H_7$ |
| 56 | 2,4,6-$(CH_3)_3$—3-$COCH_3$ | c | $C_2H_5$ | n-$C_3H_7$ |
| 57 | 2,3,4,5-$(CH_3)_4$—6-$SO_2CH_3$ | H | $C_2H_5$ | n-$C_3H_7$ |
| 58 | 2,3,4,5-$(CH_3)_4$—6-$SCH_3$ | $COCH_3$ | $C_2H_5$ | n-$C_3H_7$ |
| 59 | 2,4,6-$(CH_3)_3$—3-$CH_2SC_4H_9$—n | H | $C_2H_5$ | n-$C_3H_7$ |
| 60 | 2,4,6-$(CH_3)_3$—3-$OCF_2H$ | H | $C_2H_5$ | $C_2H_5$ |

Footnotes to Table 1
a $C_6H_5CO$
b 4-$CH_3C_6H_4SO_2$
c 4-$NO_2C_6H_4CO$

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 5-(substituted phenyl)cyclohexane-1,3-dione of formula IX. This reaction may be carried out in a two step process by condensing a benzaldehyde derivative of formula V with acetone to form a ketone of formula VI, which is in turn condensed with a malonic acid ester of formula VII to give a 5-(substituted phenyl)cyclohexane-1,3-dione of formula IX, either with or without the isolation of the intermediate of formula VIII.

Alternatively, this preparation may be carried out in a two step process by condensing a benzaldehyde derivative of formula V with a malonic acid ester of formula VII to give a benzylidenemalonate derivative of formula X which is in turn condensed with an acetoacetic acid ester of formula XI to give a 5-(substituted phenyl)-cyclohexane-1,3-dione of formula IX, either with or without isolation of the intermediate of formula XII.

In a further alternative process this preparation may be carried out by condensing a cinnamate of formula XXI with an acetoacetic acid ester of formula XI to give a 5-(substituted phenyl)cyclohexane-1,3-dione of formula IX, either with or without isolation of the intermediate of formula VIII.

The above reaction sequences are set out in SCHEME A parts (i), (ii) and (iii) respectively below, wherein R represents a $C_1$ to $C_6$ alkyl group.

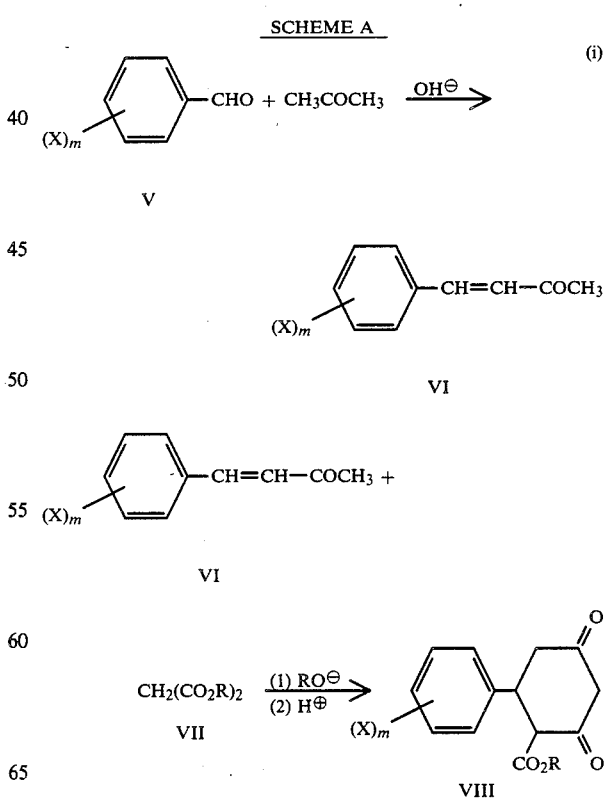

SCHEME A

-continued
SCHEME A

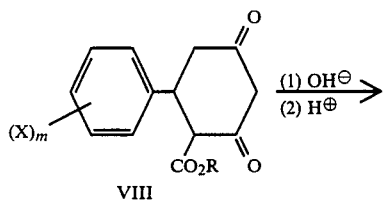

VIII

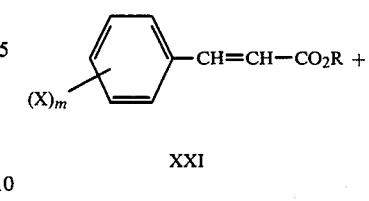

XXI

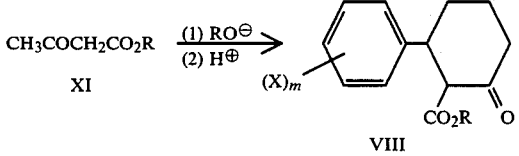

VIII

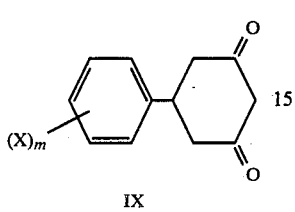

IX (ii)

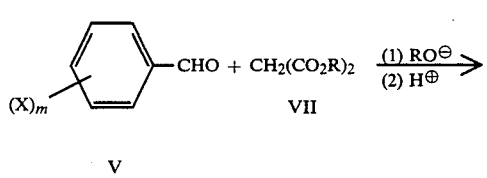

V    VII

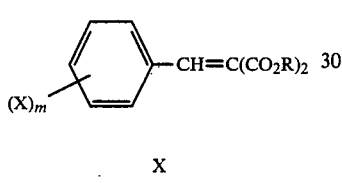

VIII

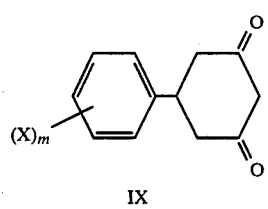

IX

X

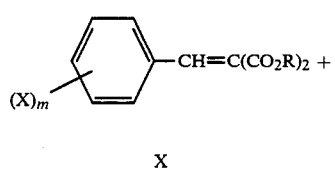

X

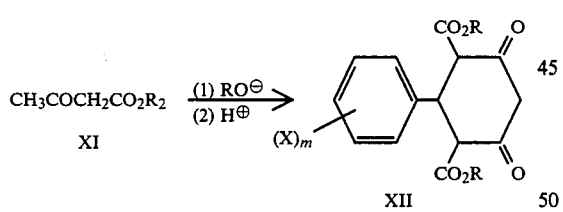

XII

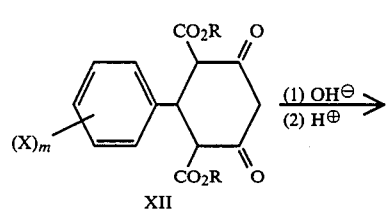

XII

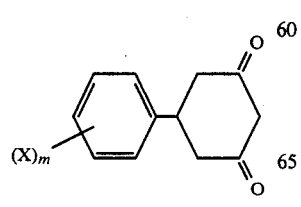

IX

Part B involves the acylation of a compound of formula IX to give a 2-acyl-5-(substituted phenyl)cyclohexane-1,3-dione of formula XIII. This reaction may be carried out by reacting a 5-(substituted phenyl)cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV; or (vii) a mixture of an acid halide of formula XV and the corresponding acid;

(viii) an alkali metal or alkaline earth metal hydride followed by reaction with an acid anhydride of formula XIV or an acid halide of formula XV.

Alternatively this reaction may be carried out by:

(ix) reacting a 5-(substituted phenyl)cyclohexane-1,3-dione of formula IX with an acid halide of formula XV in the presence of pyridine to give an intermediate O-acyl derivative of formula XVI; and then:

(x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

SCHEME B
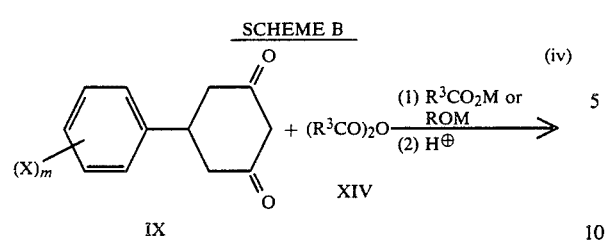
(iv)
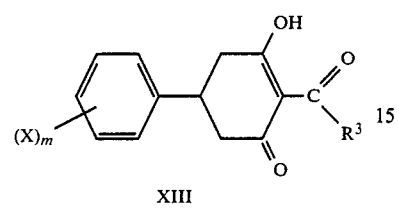
(v)
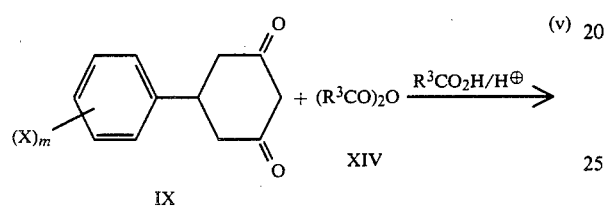
(vi)
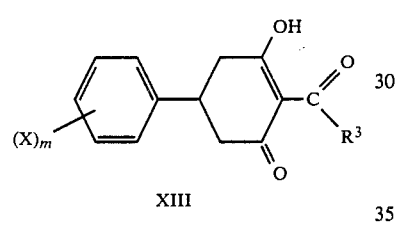
(vii)
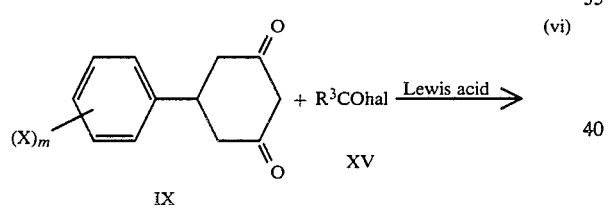
-continued
SCHEME B
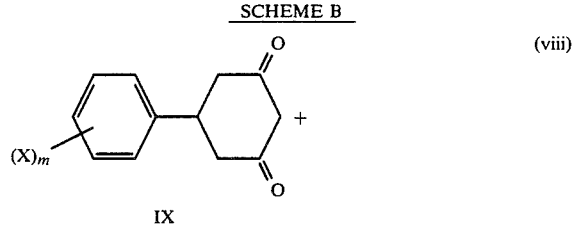
(viii)
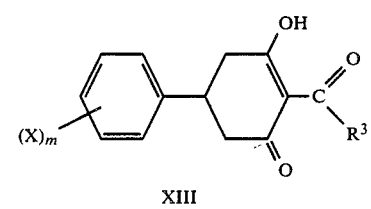
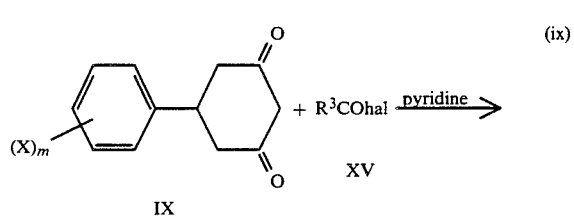
(ix)
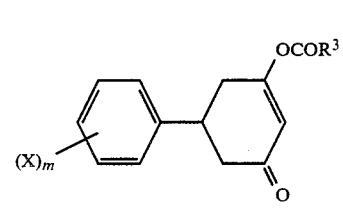
(x)
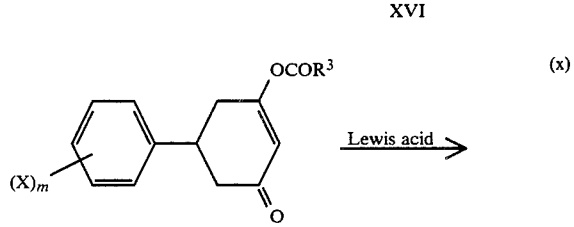
(xi)
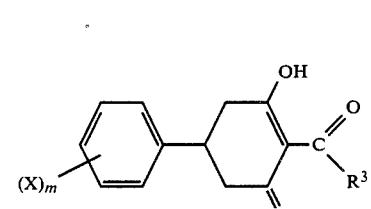
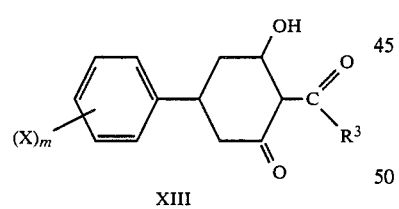
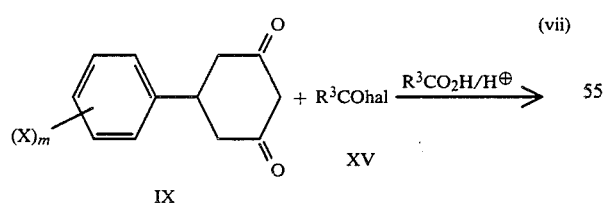
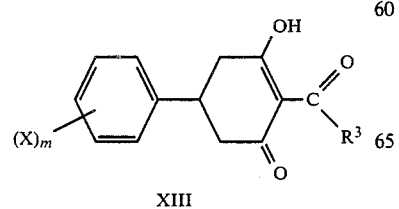
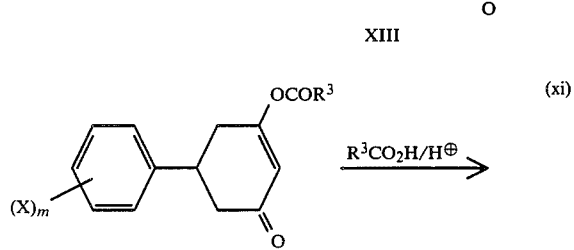

-continued
SCHEME B

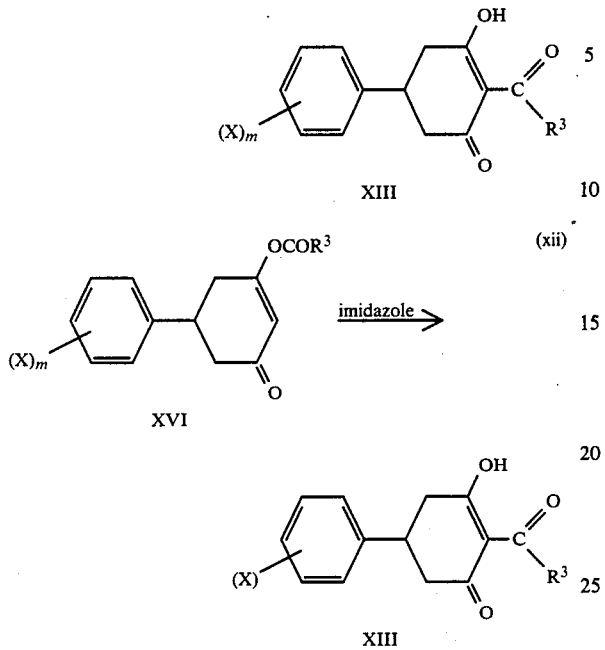

Part C involves the formation of a compound of the invention of formula I wherein $R^1$ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

SCHEME C

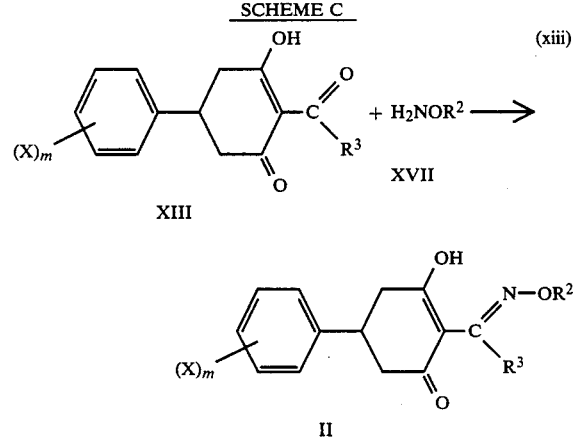

-continued
SCHEME C

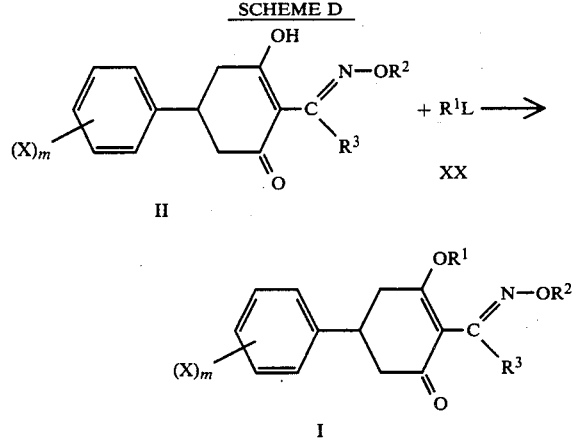

Compounds of the invention of formula I wherein $R^1$ is not hydrogen may be prepared from compounds of the invention of formula I wherein $R^1$ is hydrogen, that is, compounds of formula II, by acylation etherification or sulfonylation as required. This reaction is outlined in SCHEME D below.

SCHEME D

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, wherein X, $R^1$, $R^2$, $R^3$ and m are as hereinbefore defined, which process comprises:

(a) reacting a benzaldehyde derivative of formula V with acetone to give a ketone derivative of formula VI and reacting the ketone derivative of formula VI with malonic acid ester of formula VII, wherein R is $C_1$ to $C_6$ alkyl, to give a 5-(substituted phenyl)cyclohexane-1,3-dione derivative of formula IX; or reacting a benzaldehyde derivative of formula V with a malonic acid ester of formula VII to give a benzylidenemalonate derivative of formula X and reacting the benzylidenemalonate derivative of formula X with an acetoacetic acid ester of formula XI, wherein R is $C_1$ to $C_6$ alkyl, to give a 5-(substituted phenyl)cyclohexane-1,3-dione derivative of formula IX; or reacting a cinnamate of formula XXI, wherein R is $C_1$ to $C_6$ alkyl, with an acetoacetic acid ester of formula XI, wherein R is $C_1$ to $C_6$ alkyl, to give a 5-(substituted phenyl)cyclohexane-1,3-dione derivative of formula IX;

(b) acylating the 5-(substituted phenyl)cyclohexane-1,3-dione derivative of formula IX with an acid anhydride of formula XIV or an acid halide of formula XV to give a 2-acyl-5-(substituted phenyl)cyclohexane-1,3-dione derivative of formula XIII;

(c) reacting the 2-acyl-5-(substituted phenyl)cyclohexane-1,3-dione derivative of formula XIII with an alkoxyamine derivative of formula XVII to give a compound of the invention of formula II or reacting the 2-acyl-5-(substituted phenyl)cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and (d) reacting the compound of the invention of formula II with a compound of formula XX, wherein L is a good leaving group, to give a compound of the invention of formula I.

Certain of the intermediate compounds of formulae VI, VIII, IX, X, XII, XXI, XIII, XVI and XVIII are novel compounds and therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against monocotyledonous plants, or grasses. However, certain of the compounds of formula I are selectively active within the group of monocotyledonous plants and may be used at a rate sufficient to kill or severely damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of the present invention of formula I have three or more substituents in the phenyl ring located in the 5-position of the cyclohexane ring. Surprisingly, among the compounds of the invention which show highest herbicidal activity are those compounds of formula I in which the phenyl group is substituted in the 2- and 6-positions. More surprisingly, among the more preferred or more active compounds are those compounds of formula I in which the phenyl group is substituted in the 2-, 3- and 6-positions.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Certain of the compounds of formula I exhibit useful plant growth regulating activity. For example, while certain compounds of formula I show selective herbicidal activity against wild grasses in crops of cultivated plants, at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown by compounds of the invention include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined an an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, prophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric mateials such as, for example, ground or powdered plasstics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts, either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbidide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitriamine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)carbamate (common name phenmedipham) and 3-[(ethoxycarbony)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert- butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2- nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyl-diphenylacetamide (common name diphenamid), N-(1-naphthyl)phthalamic acid (common name naptalam) and 3-amino-1,2,4-triazole.

Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)glycine (common name glyphosate) and its salts and esters.

The invention is now illustrated by, but in no way limited to, the following Examples.

EXAMPLE 1

2-[1-(Ethoxyimino)propyl]-3-hydroxy-5-(2,4,6-trimethyl-3-nitrophenyl)cyclohex-2-en-1-one (1)

(i) An aqueous solution of 1% sodium hydroxide (29.5 ml) was added dropwise over a period of 5 minutes to a suspension of mesitylaldehyde (10.0 g; 68 mmole) in acetone (50 ml) and water (50 ml). The mixture was stirred at a temperature of 65° C. for a period of 1½ hours and then was extracted with dichloromethane (200 ml). The organic extract was washed several times with water, dried over anhydrous sodium sulfate, and the solvent was removed by evaporation under reduced pressure using a rotary evaporator. The product 1-(2,4,6-trimethylphenyl)but-1-en-3-one, a viscous oil, solidified on standing to give a white solid (11.5 g; 90%), mp 64° C. Proton magnetic resonance spectrum (CDCl$_3$; δ in ppm): 2.25 (12H, m); 6.30 (1H, d); 6.88 (2H, s); 7.64 (1H, d).

(ii) Diethyl malonate (10.1 g; 60 mmole) was added to a solution of sodium metal (1.4 g; 60 mmole) in anhydrous absolute ethanol (50 ml) and the mixture was heated to reflux temperature. A mixture of 1-(2,4,6-trimethylphenyl)but-1-en-3-one (11.4 g; 61 mmole) in anhydrous absolute ethanol (50 ml) was added over a period of 2 minutes and the mixture was heated under reflux for a period of 2 hours. An aqueous solution of sodium hydroxide (7.3 g; 180 mmole in 100 ml of water) was added and the mixture was heated under reflux for a further 4½ hours. The solution was poured into water (200 ml) and the aqueous mixture was extracted twice with ethyl acetate (100 ml). The aqueous phase was acidified with concentrated hydrochloric acid and warmed gently until the evolution of carbon dioxide ceased. The aqueous mixture was extracted with ethyl acetate, dried over anhydrous sodium sulfate, and the solvent was removed by evaporation under reduced pressure using a rotary evaporator. The product, 3-hydroxy-5-mesitylcyclohex-2-en-1-one, was obtained as a pale yellow solid (10.9 g; 77.4%), mp 165° C. Proton magnetic resonance spectrum (dimethylsulfoxide; δ in ppm): 2.0–4.1 (14H, m); 5.2 (1H, s); 6.8 (2H, s); 11.2 (1H, br.s).

(iii) (a) Propionic anhydride (15.0 ml) was added cautiously to freshly prepared sodium methoxide (0.47 g; 9 mmole). On completion of the reaction 3-hydroxy-5-mesitylcyclohex-2-en-1-one (5.0 g; 22 mmole) was added and the reaction mixture was heated under reflux at a temperature of 160° C. for a period of 2 hours. The excess propionic anhydride was removed by evaporation under reduced pressure using a rotary evaporator. Aqueous 30% sodium hydroxide solution (50 ml) was added to the residue and the mixture was heated under reflux for a period of 1 hour with vigorous stirring. After cooling the mixture was acidified with concentrated hydrochloric acid and the aqueous mixture was extracted with dichloromethane. The organic extracts were dried over anhydrous sodium sulfate and the solvent was removed by evaporation under reduced pressure using a rotary evaporator. The product, a brown oil, was purified by chromatography over silica gel (eluant dichloromethane) to give 3-hydroxy-5-mesityl-2-propionylcyclohex-2-en-1-one (3.17 g; 50.2%) as a pale yellow oil. Proton magnetic resonance spectrum (CDCl$_3$; δ in ppm): 1.60 (3H, t, J=8 Hz); 2.24. (3H, s); 2.37 (6H, s); 2.64–5.26 (7H, m), 6.84 (2H, m); 18.26 (1H, s).

(iii) (b) 3-Hydroxy-5-mesityl-2-propionylcyclohex-2-en-1-one (1.3 g; 4.5 mmole) was added to acetic anhydride (3.0 g) at 5° C. A solution of fuming nitric acid (0.42 g) in a glacial acetic acid (0.27 g)/acetic anhydride (0.27 g) solution was added to the cooled, stirred mixture dropwise over a period of 5 minutes. The mixture was maintained at 5° C. over a period of 1 hour and then at room temperature over a period of 2 hours followed by heating at 50° C. for 10 minutes. The resultant cooled solution was then poured into ice water (100 ml) and extracted with diethyl etther. The organic phase was washed three times with saturated sodium bicarbonate solution and twice with water, then dried over anhydrous sodium sulfate. The solvent was removed by evaporation under reduced pressure using a rotary evaporator and the resultant yellow solid recrystallized from ethanol to give 3-hydroxy-5-(2,4,6-trimethyl-3-nitrophenyl)-2-propionylcyclohex-2-en-1-one (0.65 g; 43.6%) as a yellow solid mp 174° C.

(iv) Ethoxyamine hydrochloride (0.26 g; 2.7 mmole) and then sodium hydroxide (0.11 g; 2.7 mmole) were added to a solution of 3-hydroxy-5-(2,4,6-trimethyl-3-nitrophenyl)-2-propionylcyclohex-2-en-1-one (0.6 g; 1.8 mmole) in absolute ethanol (150 ml). The mixture was stirred at room temperature for a period of 18 hours and then the ethanol was removed by evaporation under reduced pressure. The residue was treated with dichloromethane and the organic phase was washed twice with water and dried over anhydrous sodium sulfate. The solvent was removed by evaporation under reduced pressure to give the product, 2-[1-(ethoxyimino)-propyl]-3-hydroxy-5-(2,4,6-trimethyl-3-nitrophenyl)cyclohex-2-en-1-one (0.56 g; 83.2%) as a pale yellow oil. The product was characterized by proton nuclear magnetic resonance spectroscopy and the spectroscopic data is recorded in Table 5, Example 37.

EXAMPLE 2

2-[1-(Ethoxyimino)propyl]-3-hydroxy-5-(2,4,6-trimethyl-3,5-dinitrophenyl)cyclohex-2-en-1-one (2)

(i) 3-Hydroxy-5-mesityl-2-propionylcyclohex-2-en-1-one (2.0 g; 6.9 mmole), prepared as described in Example 1 parts (i) to (iii) (a), was added to a 1,2-dichloroethane (50 ml)/sulfuric acid (5 ml) cosolvent system at room temperature. Potassium nitrate (1.4 g; 13.8 mmole) was added in increments over 0.5 hours and the mixture was stirred at room temperature for a period of 4 hours. The mixture was then poured into ice water (200 ml) with stirring, and extracted with dichloromethane. The organic phase was washed twice with water, dried over anhydrous sodium sulfate and the solvent removed by evaporation under reduced pressure using a rotary evaporator. The product, an orange solid, was purified by chromatography over silica gel (eluant dichloromethane) to give 3-hydroxy-5-(2,4,6-trimethyl-3,5-dinitrophenyl)-2-propionylcyclohex-2-en-1-one (0.27 g; 10.3%) as a pale orange solid, mp 249° C.

(ii) Ethoxyaminehydrochloride (0.36 g, 3.7 mmole) and then sodium hydroxide (0.15 g, 3.7 mmole) were added to a solution of 3-hydroxy-5-(2,4,6-trimethyl-3,5-dinitrophenyl)-2-propionylcyclohex-2-en-1-one (1.0 g; 2.7 mmole) in absolute ethanol (80 ml). The mixture was stirred at room temperature for a period of 24 hours and then the ethanol was removed by evaporation under reduced pressure. The residue was treated with dichloromethane and the organic phase was washed twice with water and then dried over anhydrous sodium sulfate. The solvent was removed by evaporation under reduced pressure and the product recrystallized from ethanol to give 2-[1-(ethoxyimino)propyl]-3-hydroxy-5-(2,4,6-trimethyl-3,5-dinitrophenyl)cyclohex-2-en-1-one (0.45 g; 39.8%) as a white solid, mp 170° C.

EXAMPLE 3

Compounds No 6, 7, 16, 18, 23 were prepared from the appropriate 5-alkyl-2-alkanoylcyclohexane-1,3-dione by nitration and then reaction with the appropriate hydroxylamine derivative following essentially the same procedure as that described in Example 1 parts (iii)b and (iv). Each of the products was characterized by proton nuclear magnetic resonance spectroscopy and the spectroscopic data is recorded in Table 5, Example 37.

EXAMPLE 4

Compounds No 3, 4, 17, 19, 20, 21 were prepared from the appropriate 5-aryl-2-alkanoylcyclohexane-1,3-dione by nitration and then reaction with the appropriate hydroxylamine derivative following essentially the same procedure as that described in Example 2. Each of the products was characterized by proton nuclear magnetic resonance spectroscopy and the spectroscopic data is recorded in Table 5, Example 37.

EXAMPLE 5

2-[1-(Ethoxyimino)propyl]-3-hydroxy-5-(2,4,6-trimethyl-3-sulfamoylphenyl)cyclohex-2-en-1-one (12)

(i) A solution of 3-hydroxy-5-mesityl-2-propionylcyclohex-2-en-1-one (1.8 g) in chloroform (20 ml) was stirred and cooled to 0° C. during the dropwise addition of chlorosulphonic acid (10 ml). The mixture was stirred for four hours at 20° C. and then poured into ice-water and the aqueous phase was extracted with chloroform (50 ml). The organic phase was dried over anhydrous sodium sulphate and the solvent was removed by evaporation under reduced pressure using a rotary evaporator. The product 3-hydroxy-5-(2,4,6-trimethyl-3-chlorosulphonylphenyl)-2-propionylcyclohex-2-en-1-one was isolated as a brown oil (2.4 g, 97%). Proton magnetic resonance spectrum (CDCl$_3$; δ in ppm): 1.16 (3H, t); 2.47 (3H, s); 2.69 (3H, s); 2.80 (3H, s); 2.7–4.0 (7H, m); 7.05 (1H, s); 18.30 (1H, s).

(ii) A mixture of 3-hydroxy-5-(2,4,6-trimethyl-3-chlorosulphonylphenyl)-2-propionylcyclohex-2-en-1-one (1.3 g) and aqueous ammonia (50 ml, 25%) was stirred at 20° C. for 1 hour. The mixture was acidified with dilute hydrochloric acid and the product was extracted into dichloromethane (2×100 ml). The organic layer was dried over anhydrous sodium sulphate and the solvent was removed by evaporation under reduced pressure using a rotary evaporator to give 3-hydroxy-5-(2,4,6-trimethyl-3-sulfamoylphenyl)-2-propionylcyclohex-2-en-1-one (1.1 g, 81%) as a pale brown foam. Proton magnetic resonance spectrum (CDCl$_3$; δ in ppm): 1.17 (3H, t): 2.42 (3H, s); 2.63 (3H, s); 2.72 (3H, s); 2.8–4.0 (7H, m); 4.98 (2H, s); 6.96 (1H, s); 18.27 (1H, s).

(iii) Reaction of ethoxyamine hydrochloride with 3-hydroxy-5-(2,4,6-trimethyl-3-sulfamoylphenyl)-2-propionylcyclohex-2-en-one following essentially the same procedure as that described in Example 1 part (iv) gave 2-[1-(ethoxyimino)propyl]-3-hydroxy-5-(2,4,6-trimethyl-3-sulfamoylphenyl)cyclohex-2-en-1-one (12). The compound was characterized by its proton magnetic resonance spectrum which is given in Table 5, Example 37.

EXAMPLE 6

2-[1-(Ethoxyimino)propyl]-3-hydroxy-5-(2,4,6-trimethyl-3-dimethylsulfamoylphenyl)cyclohex-2-en-1-one (11) was prepared from 3-hydroxy-5-mesityl-2-propionylcyclohex-2-en-1-one, chlorosulfonic acid, dimethylamine, and ethoxyamine hydrochloride following essentially the same procedure as that described in Example 5.

2-[1-(Ethoxyimino)propyl]-3-hydroxy-5-(2,6-dimethyl-3-dimethylsulfamoylphenyl)cyclohex-2-en-1-one (5) was prepared from 3-hydroxy-5-(2,6-dimethylphenyl)-2-propionylcyclohex-2-en-1-one, chlorosulfonic acid, dimethylamine, and ethoxyamine hydrochloride following essentially the same procedure as that described in Example 5.

The compounds were characterized by proton nuclear magnetic resonance spectroscopy and the spectroscopic data is recorded in Table 5, Example 37.

EXAMPLE 7

2-[1-(Ethoxyimino)butyl]-3-hydroxy-5-(3-amino-2,4,6-trimethylphenyl)cyclohex-2-en-1-one (8)

(i) 3-Hydroxy-5-(2,4,6-trimethyl-3-nitrophenyl)-2-butyrylcyclohex-2-en-1-one was prepared by nitration of 3-hydroxy-5-(2,4,6-trimethylphenyl)-2-butyrylcyclohex-2-en-1-one following essentially the same procedure as that described in Example 1 part (iii) (b).

(ii) A solution of 3-hydroxy-5-(2,4,6-trimethyl-3-nitrophenyl)-2-butyrylcyclohex-2-en-1-one (3.3 g, 0.01 mole) and sodium hydroxide (38 g) in 50% aqueous ethanol (120 ml) was stirred and heated under reflux. Sodium dithionite (9.6 g, 0.05 mole) was added in portions over a period of 30 minutes to the solution and refluxing was continued for 1 hour. The reaction mixture was filtered while still hot and the filtrate was diluted with water (100 ml), neutralized with hydrochloric acid and finally extracted with dichloromethane (2×100 ml). Evaporation of the dichloromethane layer gave 3-hydroxy-5-(3-amino-2,4,6-trimethylphenyl)-2-butyrylcyclohex-2-en-1-one (0.96 g, 32%) as an orange oil. Proton magnetic resonance spectrum (CDCl$_3$; δ in ppm); 1.00 (3H, t); 1.5 (2H, m); 2.14 (3H,s); 2.22 (3H, s); 2.30 (3H, s); 2.4–4.0 (7H, m); 6.78 (1H, s); exchangeable protons not observed.

(iii) Reaction of 3-hydroxy-5-(3-amino-2,4,6-trimethylphenyl)-2-butyrylcyclohex-2-en-1-one with ethoxyamine hydrochloride following essentially the same procedure as described in Example 1 part (iv) gave 2-[1-(ethoxyimino)butyl]-3-hydroxy-5-(3-amino-2,4,6-trimethylphenyl)cyclohex-2-en-1-one (8) as a pale orange oil. The compound was characterized by its proton magnetic resonance spectrum which is given in Table 5, Example 37.

EXAMPLE 8

2-[1-(Ethoxyimino)propyl]-3-hydroxy-5-(3-acetamido-2,4,6-trimethylphenyl)cyclohex-2-en-1-one (25)

(i) 3-Hydroxy-5-(3-amino-2,4,6-trimethylphenyl)-2-propionylcyclohex-2-en-1-one was prepared from 3-hydroxy-5-(2,4,6-trimethylphenyl)-2-propionylcyclohex-2-en-1-one by nitration and reduction of the nitro group following essentially the same procedure as that described in Example 7 parts (i) and (ii).

(ii) A solution of 3-hydroxy-5-(3-amino-2,4,6-trimethylphenyl)-2-propionylcyclohex-2-en-1-one (2.6 g; 8.6 mmole) and pyridine (0.7 g; 9 mmole) in dichloromethane (100 ml) was treated with acetyl chloride (0.69 g; 9 mmole) at 20° C. with stirring. After 1.5 hours the mixture was poured into water (100 ml) and shaken. The organic layer was separated and dried over anhydrous magnesium sulfate and the solvent was removed under reduced pressure using a rotary evaporator. The product was purified by chromatograpy over silica gel (eluent 1% methanol in dichloromethane) to give 3-hydroxy-5-(3-acetamido-2,4,6-trimethylphenyl)-2-propionylcyclohex-2-en-1-one (1.0 g, 34%) as a pale orange semi-crystalline solid. Proton magnetic resonance spectrum (CDCl$_3$, δ in ppm): 1.20 (3H, t); 2.18 (3H, s); 2.20 (3H, s); 2.27 (3H, s); 2.35 (3H, s); 2.4–4.0 (7H, m); 6.6 (1H, bs); 6.88 (1H, s); 18.20 (1H, s).

(iii) 2-[1-(Ethoxyimino)propyl]-3-hydroxy-5-(3-acetamido-2,4,6-trimethylphenyl)cyclohex-2-en-1-one (25) was prepared from 3-hydroxy-5-(3-acetamido-2,4,6-trimethylpheny)cyclohex-2-en-1-one and ethoxyamine hydrochloride following essentially the same procedure as that described in Example 1 part (iv). The product was characterized by proton magnetic resonance spectroscopy and the spectroscopic data is reported in Table 5, Example 37.

EXAMPLE 9

2-[1-(Ethoxyimino)butyl]-3-hydroxy-5-(3-butyryl-2,4,6-trimethylphenyl)cyclohex-2-en-1-one (14)

(i) A mixture of 3-hydroxy-5-mesitylcyclohex-2-en-1-one (21.0 g, 0.091 mole), butyric anhydride (45 ml) and butyric acid (45 ml) was stirred and heated at 120° C. until homogeneous. Trifluoromethane sulphonic acid (1.0 ml) was added and the solution was heated for 1 hour at 120°–130° C. The solution was poured with stirring into ice-water, then neutralized with sodium bicarbonate and extracted with diethyl ether. The ether extract was dried over anhydrous magnesium sulphate and the drying agent was removed by filtration. The solvent was removed by evaporation under reduced pressure using a rotary evaporator and the residue was subjected to chromatography on silica gel (eluant n-hexane:chloroform (1:1)) to give 3-hydroxy-5-mesityl-2-butyrylcyclohex-2-en-1-one (14 g; 51%) as a pale yellow oil. Proton magnetic resonance spectrum (CDCl$_3$; δ in ppm): 1.00 (3H, t); 1.6 (2H, m); 2.22 (3H, s); 2.35 (6H, s); 2.4–4.0 (7H, m); 6.80 (2H, s); 18.20 (1H, s).

Later fractions gave 2-butyryl-3-hydroxy-5-(3-butyryl-2,4,6-trimethylphenyl)cyclohex-2-en-1-one (0.5 g; 1.3%) as a pale yellow oil. Proton magnetic resonance spectrum (CDCl$_3$; δ in ppm): 0.99 (6H, t); 1.4–1.9 (4H, m); 2.14 (3H, s); 2.22 (3H, s); 2.38 (3H, s); 2.4–4.0 (9H, m); 6.84 (1H, s); 18.26 (1H, s).

(ii) Reaction of ethoxyamine with 2-butyryl-3-hydroxy-5-(3-butyryl-2,4,6-trimethylphenyl)cyclohex-2-en-1-one following essentially the same procedure as that described in Example 1 part (iv) gave the title compound (14) which was characterized by its proton magnetic resonance spectrum which is given in Table 5, Example 37.

EXAMPLE 10

2-[1-(Ethoxyimino)propyl]-3-hydroxy-5-(3-propionyl-2,4,6-trimethylphenyl)cyclohex-2-en-1-one (35)

Compound No 35 was prepared from 3-hydroxy-5-mesitylcyclohex-2-en-1-one, propionic anhydride, propionic acid and ethoxyamine hydrochloride following essentially the same procedure as that described in Example 9. The product was characterized by proton nuclear magnetic resonance spectroscopy and the spectroscopic data is recorded in Table 5, Example 37.

EXAMPLE 11

2-[1-(Ethoxyimino)propyl]-3-hydroxy-5-(3-chloro-6-difluoromethoxy-2,4-dimethylphenyl)cyclohex-2-en-1-one (28)

(i) A solution of 4-chloro-3,5-dimethylphenol (16 g, 0.1 mole) in dichloromethane (100 ml) was stirred and cooled to 2° C. in an ice bath. Titanium tetrachloride (35 g, 0.18 mole) was added dropwise over a period of 10 minutes and dichloromethylmethyl ether (11.5 g, 0.1 mole) was added slowly to the dark red solution, the temperature being kept below 10° C. throughout. After the solution had been stirred at 5° C. for 30 minutes the temperature was allowed to rise and to remain at 20° C. for 30 minutes. Finally the solution was warmed at 35° C. for 15 minutes and then poured into ice water (200 ml). The mixture was shaken vigorously until almost colourless and then the dichloromethane layer was separated and the aqueous phase was extracted with more dichloromethane (2×50 ml). The combined organic layers were washed with water thoroughly (4×200 ml) and then dried over anhydrous magnesium sulphate. The drying agent was removed by filtration and the filtrate was concentrated under reduced pressure using a rotary evaporator. The product, 3-chloro-6-hydroxy-2,4-dimethylbenzaldehyde was isolated as a white solid (13 g, 70%), mp 89°–90° C. Proton magnetic resonance spectrum (CDCl$_3$; δ in ppm): 2.40 (3H, s); 2.64 (3H, s); 6.71 (1H, s); 10.23 (1H, s); 11.91 (1H, s).

(ii) A solution of sodium hydroxide (8.4 g) in water (10 ml) was added with vigorous stirring to a solution of 3-chloro-6-hydroxy-2,4-dimethylbenzaldehyde (3.6 g)

in dioxane (30 ml). A thick yellow suspension formed which was heated at 65°-75° C. while chlorodifluoromethane was bubbled in slowly with vigorous stirring. After 30 minutes the thick suspension had almost dissolved and the gas flow was stopped and heating and stirring continued for a further 10 minutes. The mixture was cooled, diluted with water (50 ml) and ether (20 ml) and then filtered to remove traces of inorganic impurities. The ether layer was separated and the aqueous layer was extracted with more ether (30 ml). The combined organic layers were washed with water (3×50 ml) and then separated and dried over anhydrous magnesium sulphate. The drying agent was removed by filtration and the solvent was evaporated under reduced pressure using a rotary evaporator. The product, 3-chloro-6-difluoromethoxy-2,4-dimethylbenzaldehyde, a colourless liquid was characterized by its proton magnetic resonance spectrum. Pmr (CDCl$_3$; $\delta$ in ppm): 2.44 (3H, s); 2.65 (3H, s); 6.53 (1H, t, J=82 Hz); 6.96 (1H, s); 10.40 (1H, s).

(iii) 3-Chloro-6-difluoromethoxy-2,4-dimethylbenzaldehyde was converted into 3-hydroxy-5-(3-chloro-6-difluoromethoxy-2,4-dimethylphenyl)cyclohex-2-en-1-one following essentially the same procedure outlined in Example 1 parts (i) and (ii). The compound was obtained as a pale yellow oil and characterized by its proton magnetic resonance spectrum (CDCl$_3$; $\delta$ in ppm): 2.36 (3H, s); 2.43 (3H, s); 2.4–4.0 (5H, m); 5.6 (2H, bs); 6.52 (1H, t), J=82 Hz); 6.82 (1H, s).

(iv) Sodium hydride (0.17 g of 50% dispersion in oil; 3.5 mmole) was added to a stirred solution of 3-hydroxy-5-(3-chloro-6-difluoromethoxy-2,4-dimethylphenyl)cyclohex-2-en-1-one (1.0 g; 3.1 mmole) in dimethyl formamide (10 ml) at 80° C. The mixture was kept at 80° C. until the evolution of hydrogen stopped and the temperature was then raised to 120° C. and propionic anhydride (0.5 ml; 3.8 mmole) was added. After 3 hours at 120° C. the mixture was poured into water (100 ml) and extracted with toluene (2×50 ml). The toluene extracts were dried over anhydrous magnesium sulphate and the solvent was removed by evaporation under reduced pressure using a rotary evaporator. The product was purified by chromatography over silica gel (eluant chloroform) to give 3-hydroxy-5-(3-chloro-6-difluoromethoxy-2,4-dimethylphenyl)-2-propionylcyclohex-2-en-1-one as a colourless oil (0.46 g; 39%). Proton magnetic resonance spectrum (CDCl$_3$; $\delta$ in ppm): 1.20 (3H, t); 2.35 (3H, s); 2.43 (3H, s); 2.4–4.0 (7H, m); 6.54 (1H, t, J=82 Hz); 6.85 (1H, s); 18.25 (1H, s).

(v) 2-[1-(ethoxyimino)propyl]-3-hydroxy-5-(3-chloro-6-difluoromethoxy-2,4-dimethylphenyl)cyclohex-2-en-1-one was prepared from 3-hydroxy-5-(3-chloro-6-difluoromethoxy-2,4-dimethylphenyl)-2-propionylcyclohex-2-en-1-one and ethoxyamine hydrochloride following essentially the same procedure as that described in Example 1 part (iv). The product was characterized by proton magnetic resonance spectroscopy and the spectroscopic data is reported in Table 5, Example 37.

EXAMPLE 12

Compounds Nos. 42 and 60 (see Table 1) were prepared from the appropriate phenol following essentially the same procedure as that described in Example 11, parts (i) to (v), except that butyric anhydride was used instead of propionic anhydride. The product was characterized by proton nuclear magnetic resonance spectroscopy and the spectroscopic data is reported in Table 5, Example 37.

EXAMPLE 13

2-[1-(Ethoxyimino)propyl]-3-hydroxy-5-(3-methylsulfinyl-2,4,6-trimethylphenyl)cyclohex-2-en-1-one (9) and 2-[1-(ethoxyimino)propyl]-3-hydroxy-5-(3-methylsulfonyl-2,4,6-trimethylphenyl)cyclohex-2-en-1-one (10)

(i) 3-Hydroxy-5-(2,4,6-trimethyl-3-methylthiophenyl)-2-propionylcyclohex-2-en-1-one was prepared from 2,4,6-trimethyl-3-methylthiobenzaldehyde following essentially the same procedure described in Example 1, parts (i), (ii) and (iii) (a).

(ii) 3-Chloroperbenzoic acid (1.5 g, 8 mmole) was added with stirring at 5° C. to a solution of 3-hydroxy-5-(2,4,6-trimethyl-3-methylthiophenyl)-2-propionylcyclohex-2-en-1-one (2.5 g; 7.5 mmole) in dichloromethane (50 ml). The solution was left at 20° C. for 16 hours then washed with aqueous bicarbonate solution. The organic layer was then dried over anhydrous magnesium sulphate and the solvent was removed by evaporation under reduced pressure using a rotary evaporator. The resultant oil was chromatographed over silica gel (eluant chloroform) to give first 3-hydroxy-5-(2,4,6-trimethyl-3-methylsulfonylphenyl)-2-propionylcyclohex-2-en-1-one (1.1 g; 40%) and then secondly 3-hydroxy-5-(2,4,6-trimethyl-3-methylsulfinylphenyl)-2-propionylcyclohex-2-en-1-one (0.20 g; 8%) both as pale yellow oils which were characterized by their proton magnetic resonance spectra which were respectively (CDCl$_3$; $\delta$ in ppm): 1.16 (3H, t); 2.43 (3H, s), 2.61 (3H, s); 2.70 (3H, s); 3.10 (3H, s); 2.4–4.0 (7H, m); 7.00 (1H, s); 18.2 (1H, bs) and 1.17 (3H, t); 2.40 (3H, s); 2.54 (3H, s); 2.65 (3H, s); 2.86 (3H, s); 2.40–4.0 (7H, m); 6.88 (1H, s); 18.2 (1H, bs).

(iii) The title compounds (9) and (10) were prepared from the appropriate 3-hydroxy-5-(substituted phenyl)-2-propionylcyclohex-2-en-1-one derivative and ethoxyamine hydrochloride following essentially the same procedure as that described in Example 1 part (iv). Each product was characterized by proton magnetic resonance spectroscopy and the spectroscopic data is recorded in Table 5, Example 37.

EXAMPLE 14

2-[1-(Ethoxyimino)butyl]-3-hydroxy-5-[3-(ethoxyimino)methyl-2,4,6-trimethylphenyl]cyclohex-2-en-1-one (15)

(i) To a solution of 2-butyryl-3-hydroxy-5-mesitylcyclohex-2-en-1-one (1.20 g) in dichloroethane (20 ml) at 0° C. was added titanium tetrachloride (3.00 g) over a period of 3 minutes. While the solution was stirred and cooled dichloromethyl methyl ether (0.46 g) in dichloroethane (20 ml) was added dropwise over a 25 minute period. After the addition was complete, the mixture was stirred for 5 minutes at 0° C., for 30 minutes at room temperature and for 2 hours under reflux. The cooled reaction mixture was poured into a separatory funnel containing crushed ice and was shaken thoroughly. The organic layer was separated, and the aqeuous solution was extracted with methylene chloride. The combined organic solution was washed with water, dried over anhydrous sodium sulfate and evaporated to dryness to give a crude brown oil (0.70 g). Purification by column chromatography over silica gel (eluant dichloromethane) gave 2-butyryl-3-hydroxy-5-(3-formyl-2,4,6-trimethylphenyl)cyclohex-2-en-1-one (0.35 g) as a pale yellow oil. Proton nuclear magnetic resonance spectrum (CDCl$_3$; δ in ppm): 1.0 (3H, t); 1.68 (2H, m); 2.43 (3H, s); 2.48 (3H, s); 2.61 (3H, s); 2.65–4.20 (7H, m); 6.94 (1H, s); 10.54 (1H, s); 18.33 (1H, s).

(ii) Ethoxyamine hydrochloride (0.20 g) and then a solution of sodium hydroxide (0.086 g) in water (1.0 ml) were added to a stirred mixture of 2-butyryl-3-hydroxy-5-(3-formyl-2,4,6-trimethylphenyl)cyclohex-2-en-1-one (0.35 g) and ethanol. The mixture was stirred at room temperature for 12 hours, then the ethanol was removed by evaporation and the residue extracted with dichloromethane. The organic extract was washed with aqueous 5% hydrochloric acid, then with water, and dried over anhydrous sodium sulfate. Evaporation of the solvent and purification by column chromatography over silica gel (eluant dichloromethane) gave 2-[1-(ethoxyimino)butyl]-3-hydroxy-5-[3-(ethoxyimino)methyl-2,4,6-trimethylphenyl]cyclohex-2-en-1-one (0.15 g) as a pale yellow oil. The product was characterized by proton nuclear magnetic resonance spectroscopy and the spectroscopic data is recorded in Table 5, Example 37.

EXAMPLE 15

2-[1-(Ethoxyimino)butyl]-3-hydroxy-5-(3-cyano-2,4,6-trimethylphenyl)cyclohex-2-en-1-one (26)

(i) A solution of 2-butyryl-3-hydroxy-5-(3-formyl-2,4,6-trimethylphenyl)cyclohex-2-en-1-one (1.50 g) and hydroxylamine hydrochloride (0.35 g) in 98% formic acid (7 ml) was refluxed for an hour and then allowed to cool. The mixture was diluted with ice water and the precipitate collected. Purification by column chromatography over silica gel (eluant dichloromethane) gave 2-butyryl-3-hydroxy-5-(3-cyano-2,4,6-trimethylphenyl)cyclohex-2-en-1-one (0.67 g; 44%) as a pale yellow oil. Proton nuclear magnetic resonance spectrum (CDCl$_3$; δ in ppm): 1.00 (3H, t); 1.68 (2H, m); 2.45 (6H, s); 2.60 (3H, s); 2.65–4.20 (7H, m); 7.42 (1H, s); 18.35 (1H, s).

(ii) 2-[1-(Ethoxyimino)butyl]-3-hydroxy-5-(3-cyano-2,4,6-trimethylphenyl)cyclohex-2-en-1-one (26) was prepared from 2-butyryl-3-hydroxy-5-(3-cyano-2,4,6-trimethylphenyl)cyclohex-2-en-1-one and ethoxyamine hydrochloride following the same procedure as that described in Example 1 part (iv). The product was characterized by proton magnetic resonance spectroscopy and the spectroscopic data is recorded in Table 5, Example 37.

EXAMPLE 16

5-(3-Acetyl-2,4,6-trimethylphenyl)-2-[1-(ethoxyimino)propyl]-3-hydroxycyclohex-2-en-1-one (13)

(i) An aqueous solution of 1% sodium hydroxide (35.7 ml) was added dropwise over a period of 5 minutes to a suspension of 3-acetyl-2,4,6-trimethylbenzaldehyde (see Example 34) (17.0 g; 89 mmole) in acetone (150 ml) and water (100 ml). The mixture was stirred at a temperature of 65° C. for a period of 1½ hour and then extracted with dichloromethane. The organic extract was washed several times with water, dried over anhydrous sodium sulfate, and the solvent was removed by evaporation under reduced pressure using a rotary evaporator. The product, 1-(3-acetyl-2,4,6-trimethylphenyl)but-1-en-3-one (14.6 g; 71.3%) was a brown viscous oil. Proton magnetic resonance spectrum (CDCl$_3$; δ in ppm): 2.20 (6H, s); 2.24 (3H, s); 2.38 (3H, s); 2.45 (3H, s); 6.20 (1H, d); 6.90 (1H, s); 7.60 (1H, d).

(ii) Diethyl malonate (10.16 g; 69 mmole) was added to a solution of sodium metal (1.46 g; 63 mmole) in anhydrous absolute ethanol (50 ml) and the mixture was heated to reflux temperature. A mixture of 1-(3-acetyl-2,4,6-trimethylphenyl)but-1-en-3-one (14.60 g; 63 mmole) in anhydrous absolute ethanol (50 ml) was added over a period of 2 minutes and the mixture was heated under reflux for a period of 2 hours. A 30% aqueous solution of sodium hydroxide (100 ml) was added and the mixture was heated under reflux for a further 4½ hours. The solution was poured into water (200 ml) and the aqueous mixture was washed with diethyl ether (2×100 ml). The aqueous phase was acidified with concentrated hydrochloric acid and warmed gently until the evolution of carbon dioxide ceased. The aqueous mixture was extracted with ethyl acetate, dried over anhydrous sodium sulfate, and the solvent was removed by evaporation under reduced pressure. The product, 5-(3-acetyl-2,4,6-trimethylphenyl)-3-hydroxycyclohex-2-en-1-one (13.55 g; 84.0%), was obtained as a glassy solid. Proton magnetic resonance spectrum (D$_6$-dimethylsulfoxide; δ in ppm): 2.20 (3H, s); 2.24 (3H, s); 2.38 (3H, s); 2.45 (3H, s); 2.45–3.40 (4H, m); 3.90 (1H, m); 5.25 (1H, s); 6.85 (1H, s); 11.0 (1H, br. s).

(iii) Sodium hydroxide (60%, 0.86 g; 22 mmole) was added to a stirred solution of 5-(3-acetyl-2,4,6-trimethylphenyl)-3-hydroxycyclohex-2-en-1-one (500 g; 20 mmole) in dimethylformamide (100 ml) at 60° C. After 15 minutes propionic anhydride (2.58 g; 22 mmole) was added and the mixture was heated at 110°–120° C. for 3 hours. The mixture was then poured into water (300 ml) and extracted with diethyl ether (2×100 ml). The ether extracts were dried over anhydrous sodium sulfate and the solvent was removed by evaporation under reduced pressure. The residue was purified by chromatography over silica gel (eluant dichloromethane) to give 5-(3-acetyl-2,4,6-trimethylphenyl)-3-hydroxy-2-propionylcyclohex-2-en-1-one (2.36 g; 37.8%) as an orange oil. The product was characterized by proton magnetic resonance spectroscopy and the spectroscopic data is reported in Table 4, Example 36.

(iv) 5-(3-Acetyl-2,4,6-trimethylphenyl)-2-[1-(ethoxyimino)propyl]-3-hydroxycyclohex-2-en-1-one (13) was prepared from 5-(3-acetyl-2,4,6-trimethylphenyl)-3-hydroxy-2-propionylcyclohex-2-en-1-one and ethoxyamine hydrochloride following essentially the same procedure as that described in Example 1, part (iv). The product was characterized by proton magnetic resonance spectroscopy and the spectroscopic data is reported in Table 5, Example 37.

EXAMPLE 17

Compounds Nos. 22, 24, 27, 29, 30, 49 and 50 (see Table 1) were prepared from the appropriate benzaldehyde derivative (see Example 34) following essentially the same procedure as that described in Example 16, parts (i) to (iv). Each of the products was characterized by proton nuclear magnetic resonance spectroscopy and the spectrosopic data is recorded in Table 5, Example 37.

EXAMPLE 18

Compounds Nos 32, 33, 38, 39, 40, 43, 48 and 52 (see Table 1) were prepared from the appropriate 5-arylcyclohexane-1,3-dione (see Example 35), butyric anhydride and ethoxyamine hydrochloride following essentially the same procedure as that described in Example 16, parts (iii) and (iv). Each of the products was characterized by proton nuclear magnetic resonance spectroscopy and the spectroscopic data is recorded in Table 5, Example 37.

EXAMPLE 19

Compounds Nos. 45 and 53 (see Table 1) were prepared from 2-butyryl-3-hydroxy-5-(2,3,4,5-tetramethyl-6-thiomethylphenyl)cyclohex-2-en-1-one (see Example 36) and the appropriate hydroxylamine hydrochloride derivative following essentially the same procedure as that described in Example 1, part (iv). Each of the products was characterized by proton nuclear magnetic resonance and the spectroscopic data is recorded in Table 5, Example 37.

EXAMPLE 20

Sodium salt of 5-(3-acetyl-2,4,6-trimethylphenyl)-2-[1-(ethoxyimino)-butyl]-3-hydroxy-cyclohex-2-en-1-one (54)

Aqueous 1% sodium hydroxide solution (3.6 ml) was added to a solution of 5-(3-acetyl-2,4,6-trimethyl-phenyl)-2-[1-(ethoxyimino)butyl]-3-hydroxycyclohex-2-en-1-one (0.33 g; 0.9 mmole) in acetone (10 ml). The solvent was removed under reduced pressure using a rotary evaporator to yield the title compound as a pale yellow solid (0.36 g; 100%), mp 198° C. (decomp.).

EXAMPLE 21

Sodium salt of 2-[1-(ethoxyimino)butyl]-3-hydroxy-5-(2,3,4,5-tetramethyl-6-thiomethylphenyl)cyclohex-2-en-1-one (44)

Compound No. 44 was prepared from compound No 32 (see Table 1) following essentially the same procedure as that described in Example 20. The title compound was isolated as a light brown solid, mp >265° C.

EXAMPLE 22

5-(3-Acetyl-2,4,6-trimethylphenyl)-2-[1-(ethoxyimino)-butyl]-3-(4-nitrobenzoyl)oxy-cyclohex-2-en-1-one (56)

The sodium salt of 5-(3-acetyl-2,4,5-trimethylphenyl)-2-[1-(ethoxyimino)butyl]-3-hydroxy-cyclohex-2-en-1-one (0.13 g; 0.33 mmole) was dissolved in acetone and then 4-nitrobenzoyl chloride (0.06 g; 0.33 mmole) was added. The mixture was stirred for 15 minutes and then the solvent was removed by evaporation under reduced pressure using a rotary evaporator. The product was purified by column chromatography over silica gel (eluant dichloromethane) to give 5-(3-acetyl-2,4,6-trimethylphenyl)-2-[1-(ethoxyimino)butyl]-3-(4-nitrobenzoyl)oxy-cyclohex-2-en-1-one (0.16 g; 93.6%) as a yellow oil.

The product was characterized by proton nuclear magnetic resonance spectroscopy and the spectroscopic data is recorded in Table 5, Example 37.

EXAMPLE 23

Compounds No. 47 and 58 were prepared from the sodium salt of 2-[1-(ethoxyimino)butyl]-3-hydroxy-5-(2,3,4,5-tetramethyl-6-thiomethylphenyl)cyclohex-2-en-1-one and the appropriate acid chloride following essentially the same procedure as that described in Example 22. Each of the products was characterized by proton nuclear magnetic resonance spectroscopy and the spectroscopic data is recorded in Table 5, Example 37.

EXAMPLE 24

5-(3-Acetyl-2,4,6-trimethylphenyl)-2-[1-(ethoxyimino)-butyl]-3-(4-toluenesulfonyl)oxy-cyclohex-2-en-1-one (55)

The sodium salt of 5-(3-acetyl-2,4,6-trimethyl-phenyl)-2-[1-(ethoxyimino)butyl]-3-hydroxy-cyclohex-2-en-1-one (0.10 g; 0.26 mmole) was dissolved in acetone and then 4-toluenesulfonyl chloride (0.05 g; 0.26 mmole) was added. The mixture was stirred for 15 minutes and then the solvent was removed by evaporation under reduced pressure using a rotary evaporator. The product was purified by column chromatography over silica gel (eluant dichloromethane) to give 5-(3-acetyl-2,4,6-trimethylphenyl)-2-[1-(ethoxyimino)butyl]-3-(4-toluenesulfonyl)oxy-cyclohex-2-en-1-one (0.13 g; 95.6%) as a yellow oil.

The product was characterized by proton nuclear magnetic resonance spectroscopy and the spectroscopic data is recorded in Table 5, Example 37.

EXAMPLE 25

Copper salt of 2-[1-(ethoxyimino)butyl]-3-hydroxy-5-(2,3,4,5-tetramethyl-6-thiomethylphenyl)cyclohex-2-en-1-one (46)

2-[1-(Ethoxyimino)butyl]-3-hydroxy-5-(2,3,4,5-tetramethyl-6-thiomethylphenyl)cyclohex-2-en-1-one (0.37 g, 0.92 mmole) in diethyl ether (50 ml) was shaken with a saturated aqueous cupric acetate solution (50 ml). The mixture was then evaporated to dryness under reduced pressure. The solid residue was washed successively with hot water, cold water and diethyl ether, then dried to give the copper salt of 2-[1-(ethoxyimino)-butyl]-3-hydroxy-5-(2,3,4,5-tetramethyl-6-thiomethyl-phenyl)cyclohex-2-en-1-one (0.25 g; 31.0%) as a pale green solid, mp 150° C. (decomp.).

EXAMPLE 26

2-[1-(Ethoxyimino)butyl]-5-(3-ethoxymethyl-2,4,6-trimethylphenyl)-3-hydroxycyclohex-2-en-1-one (41)

(i) Iodotrimethylsilane (0.5 ml) was added to a solution of 2-butyryl-3-hydroxy-5-(3-methoxymethyl-2,4,6-trimethylphenyl)cyclohex-2-en-1-one (1.50 g; 4.36 mmole) (see Example 36) in dry acetonitrile (10 ml) under nitrogen and the mixture was stirred at room temperature for 15 minutes. The solvent was evaporated and the residue was stirred with an ethanolic potassium hydroxide solution at room temperature for 15 hours. The solution was poured into dilute hydrochloric acid and then extracted with diethyl ether. The ether extract was dried over anhydrous magnesium sulfate and evaporated under reduced pressure. Purification by column chromatography over silica gel (eluant dichloromethane) gave 2-butyryl-5-(3-ethoxymethyl-2,4,6-trimethylphenyl)-3-hydroxycyclohex-2-en-1-one (1.32 g; 84.7%) as an oil.

The product was characterized by proton nuclear magnetic resonance spectroscopy and the spectroscopic data is recorded in Table 4, Example 36.

(ii) 2-[1-Ethoxyimino)butyl]-5-(3-ethoxymethyl-2,4,6-trimethylphenyl)-3-hydroxycyclohex-2-en-1-one (41) was prepared from 2-butyryl-5-(3-ethoxymethyl-2,4,6-trimethylphenyl)-3-hydroxycyclohex-2-en-1-one and ethoxyamine hydrochloride following essentially the same procedure as that described in Example 1, part (iv). The product was characterized by proton magnetic resonance spectroscopy and the spectroscopic data is reported in Table 5, Example 37.

EXAMPLE 27

2-[1-(Ethoxyimino)butyl]-3-hydroxy-5-(3-hydroxymethyl-2,4,6-trimethylphenyl)cyclohex-2-en-1-one (51)

(i) Iodotrimethylsilane (0.3 ml) was added to a solution of 2-butyryl-3-hydroxy-5-(3-methoxymethyl-2,4,6-trimethylphenyl)cyclohex-2-en-1-one (0.5 g, 1.45 mmole) (see Example 36) in dry acetonitrile (10 ml) under nitrogen and the mixture was stirred at room temperature for 15 minutes. An aqueous solution of silver nitrate was added and the mixture was stirred for a further 4 hours. The solvent was evaporated and the residue was washed successively with dilute aqueous sodium hydroxide and acetic acid, then dissolved in ethyl acetate and dried over anhydrous sodium sulfate. Evaporation under reduced pressure yielded 2-butyryl-3-hydroxy-5-(3-hydroxymethyl-2,4,6-trimethylphenyl)-cyclohex-2-en-1-one (0.42 g; 87.0%) as an oil.

The product was characterized by proton nuclear magnetic resonance spectroscopy and the spectroscopic data is recorded in Table 4, Example 36.

(ii) 2-[1-(Ethoxyimino)butyl]-3-hydroxy-5-(3-hydroxymethyl-2,4,6-trimethylphenyl)cyclohex-2-en-1-one (51) was prepared from 2-butyryl-3-hydroxy-5-(3-hydroxymethyl-2,4,6-trimethylphenyl)cyclohex-2-en-1-one and ethoxyamine hydrochloride following essentially the same procedure as that described in Example 1, part (iv).

The product was characterized by proton magnetic magnetic resonance spectroscopy and the spectroscopic data is reported in Table 5, Example 37.

EXAMPLE 28

5-[3-(n-Butylthiomethyl)-2,4,6-trimethylphenyl]-2-[1-(ethoxyimino)butyl]-3-hydroxycyclohex-2-en-1-one (59)

(i) Iodotrimethylsilane (0.3 ml) was added to a solution of 2-butyryl-3-hydroxy-5-(3-methoxymethyl-2,4,6-trimethylphenyl)cyclohex-2-en-1-one (0.5 g) (see Example 36) in dry acetonitrile (10 ml) under nitrogen, and the mixture was stirred at room temperature for 15 minutes. The solvent was evaporated and the residue was added to a solution of sodium n-butylthiolate (1.3 equivalents) in ethanol (20 ml). The mixture was stirred at room temperature for 24 hours, then poured into dilute hydrochloric acid and extracted with diethyl ether. The ether extract was dried over anhydrous sodium sulfate and then evaporated under reduced pressure. The residue was purified by column chromatography over silica gel (eluant dichloromethane) to give 2-butyryl-5-[3-(n-butylthiomethyl)-2,4,6-trimethylphenyl]-3-hydroxycyclohex-2-en-1-one (0.46 g; 79.5%) as an oil.

The product was characterized by proton nuclear magnetic resonance spectroscopy and the spectroscopic data is recorded in Table 4, Example 36.

(ii) 5-[3-(n-Butylthiomethyl)-2,4,6-trimethylphenyl]-2-[1-(ethoxyimino)butyl]-3-hydroxycyclohex-2-en-1-one (59) was prepared from 2-butyryl-5-[3-(n-butylthiomethyl)-2,4,6-trimethylphenyl]-3-hydroxycyclohex-2-en-1-one and ethoxyamine hydrochloride following essentially the same procedure as that described in Example 1, part (iv).

The product was characterized by proton magnetic resonance spectroscopy and the spectroscopic data is reported in Table 5, Example 37.

EXAMPLE 29

5-(2,6-Dimethyl-4-hydroxyphenyl)-2-[1-(ethoxyimino)propyl]-3-hydroxycyclohex-2-en-1-one (31)

(i) Palladium on activated carbon (0.30 g), followed by concentrated hydrochloric acid (20 ml), were added to a solution of 5-(4-benzyloxy-2,6-dimethylphenyl)-3-hydroxy-2-propionylcyclohex-2-en-1-one (see Example 36) (3.22 g; 8.5 mmole) in ethyl acetate (200 ml). The mixture was hydrogenated at atmospheric pressure for 3 hours, then filtered, washed with water and dried over anhydrous sodium sulfate. Evaporation of the solvent gave 5-(2,6-dimethyl-4-hydroxyphenyl)-3-hydroxy-2-propionylcyclohex-2-en-1-one (2.45 g; 100%) as a yellow oil.

The product was characterized by proton nuclear magnetic resonance spectroscopy and the spectroscopic data is recorded in Table 4, Example 36.

(ii) 5-(2,6-Dimethyl-4-hydroxyphenyl)-2-[1-(ethoxyimino)propyl]-3-hydroxycyclohex-2-en-1-one (31) was prepared from 5-(2,6-dimethyl-4-hydroxyphenyl)-3-hydroxy-2-propionylcyclohex-2-en-1-one and ethoxyamine hydrochloride following essentially the same procedure as that described in Example 1, part (iv). The product was characterized by proton nuclear magnetic resonance spectroscopy and the spectroscopic data is reported in Table 5, Example 37.

EXAMPLE 30

5-(2,4-Dimethyl-6-hydroxyphenyl)-2-[1-(ethoxyimino)butyl]-3-hydroxycyclohex-2-en-1-one (37)

Compound No 37 was prepared from 5-(6-benzyloxy-2,4-dimethylphenyl)-2-butyryl-3-hydroxycyclohex-2-en-1-one (see Example 36) following essentially the same procedure as that described in Example 29. The product was characterized by proton nuclear magnetic resonance spectroscopy and the spectroscopic data is recorded in Table 5, Example 37.

EXAMPLE 31

5-(4-Acetyloxy-2,6-dimethylphenyl)-2-[1-(ethoxyimino)propyl]-3-hydroxycyclohex-2-en-1-one (34)

(i) Acetyl chloride (0.39 g; 4.9 mmole) in dichloromethane (5 ml) was added to a solution of 5-(2,6-dimethyl-4-hydroxyphenyl)-3-hydroxy-2-propionylcyclohex-2-en-1-one (1.29 g; 4.5 mmole) and pyridine (0.39 g; 4.9 mmole) in dichloromethane (100 ml) at room temperature. The mixture was stirred for 24 hours, then poured into water and extracted with dichloromethane. The organic extract was washed with water, dried over anhydrous sodium sulfate and evaporated under reduced pressure to give an oily residue. Purification by column chromatography over silica gel (eluant dichloromethane) gave 5-(4-acetyloxy-2,6-dimethylphenyl)-3-hydroxy-2-propionylcyclohex-2-en-1-one (0.63 g; 42.0% ) as a pale cream solid.

The product was characterized by proton nuclear magnetic spectroscopy and the spectroscopic data is recorded in Table 4, Example 36.

(ii) 5-(4-Acetyloxy-2,6-dimethylphenyl)-2-[1-(ethoxyimino)propyl]-3-hydroxy-cyclohex-2-en-1-one (34) was prepared from 5-(4-acetyloxy-2,6-dimethylphenyl)-3-hydroxy-2-propionylcyclohex-2-en-1-one and ethoxyamine hydrochloride following essentially the same procedure as that described in Example 1, part (iv). The product was characterized by proton nuclear magnetic resonance spectroscopy and the spectroscopic data is recorded in Table 5, Example 37.

EXAMPLE 32

2-[1-(Ethoxyimino)butyl]-3-hydroxy-5-(4-hydroxy-2,3,6-tetramethylphenyl)cyclohex-2-en-1-one (36)

Palladium on activated carbon (0.14 g), followed by concentrated hydrochloric acid (2 drops), were added to a solution of 5-(4-benzyloxy-2,3,5,6-tetramethylphenyl)-2-[1-(ethoxyimino)butyl]-3-hydroxycyclohex-2-en-1-one (see Example 37) (1.40 g; 3.0 mmole) in ethyl acetate (50 ml). The mixture was hydrogenated at atmospheric pressure for 2 hours, then filtered, washed with water and dried over anhydrous sodium sulfate. Evaporation of the solvent gave an oily residue, which was purified by column chromatography over silica gel (eluant dichloromethane) to give 2-[1-(ethoxyimino)-butyl]-3-hydroxy-5-(4-hydroxy-2,3,5,6-tetramethylphenyl)cyclohex-2-en-1-one (0.34 g; 30.1%) as a colourless solid, mp 134° C.

EXAMPLE 33

2-[1-(Ethoxyimino)butyl]-3-hydroxy-5-(6-methylsulfonyl-2,3,4,5-tetramethylphenyl)cyclohex-2-en-1-one (57)

(i) m-Chloroperbenzoic acid (2.30 g; 13.3 mmole) was added to a solution of 2-butyryl-3-hydroxy-5-(2,3,4,5-tetramethyl-6-thiomethylphenyl)cyclohex-2-en-1-one (see Example 36) (1.63 g; 5.42 mmole) in dichloromethane (45 ml). The mixture was stirred at room temperature for 12 hours and then evaporated under reduced pressure. The residue was purified by column chromatography over silica gel (eluant dichloromethane) to give 2-butyryl-3-hydroxy-5-(6-methylsulfonyl-2,3,4,5-tetramethylphenyl)cyclohex-2-en-1-one (1.57 g; 88.0%) as a colourless solid, mp 132° C.

(ii) 2-[1-(Ethoxyimino)butyl]-3-hydroxy-5-(6-methylsulfonyl-2,3,4,5-tetramethylphenyl)cyclohex-2-en-1-one (57) was prepared from 2-butyryl-3-hydroxy-5-(6-methylsulfonyl-2,3,4,5-tetramethylphenyl)cyclohex-2-en-1-one and ethoxyamine hydrochloride following essentially the same procedure as that described in Example 1, part (iv). The product was characterized by proton nuclear magnetic resonance spectroscopy and the spectroscopic data is reported in Table 5, Example 37.

EXAMPLE 34

This example details the preparation of the benzaldehydes of formula V which were used in the preparation of the compounds of the invention of formula I.

Method A

The benzaldehydes were prepared by direct formylation following the general method described by A Rieche et al (Organic Synthesis, Vol. 5, page 49). The products were characterized by proton magnetic resonance spectroscopy and the details are recorded in Table 2 below.

Method B

See Example 11. The products were characterized by proton magnetic resonance spectroscopy and the details are recorded in Table 2 below.

Method C

The benzaldehydes were prepared from the corresponding bromobenzene following the general method described by G A Olah et al (Angew. Chem. Int. Ed. 20(10), 878, 1981). The products were characterized by proton magnetic resonance spectroscopy and the details are recorded in Table 2 below.

TABLE 2

$(X)_m$—C$_6$H$_3$—CHO     V

| $(X)_m$ | Method | Appearance | Proton Chemical Shift δ in ppm (CDCl$_3$) |
|---|---|---|---|
| 2,4,6-(CH$_3$)$_3$—3-COCH$_3$ | A | Pale Yellow solid; mp 65–67° C. | 2.20(3H,s); 2.22 (3H,s); 2.40(3H s); 2.53(3H,s); 6.40(1H,s); 10.50 (1H,s). |
| 2,4,6-(CH$_3$)$_3$—3-COCH$_3$—5-C$_2$H$_5$ | A | Yellow oil | 1.10(3H,t); 2.20 (3H,s); 2.25(3H,s); 2.38(3H,s); 2.40 (3H,s); 2.70(2H,q); 10.60(1H,s). |
| 2,3,5,6-(CH$_3$)$_4$—4-COCH$_3$ | A | Yellow oil | 2.00(6H,s); 2.20 (6H,s); 2.40(3H,s); 6.90(1H,s); 10.60 (1H,s). |
| 2,3,4,6-(CH$_3$)$_4$—5-COCH$_3$ | A | Yellow oil | 2.00–2.60(15H,M); 10.45(1H,s). |
| 3-Cl—6-OCF$_2$H—2,4-(CH$_3$)$_2$ | B | Colourless liquid | 2.44(3H,s); 2.65 (3H,s); 6.53(1H, t,J=82Hz); 6.96 (1H,s); 10.40 (1H,s). |
| 2,3,4,5-(CH$_3$)$_4$—6-SCH$_3$ | A | Brown solid; mp <50° C. | 2.16(3H,s); 2.17 (3H,s); 2.23(3H,s); 2.30(3H,s); 2.50 (3H,s); 10.58(1H, s). |
| 2,3,5,6-(CH$_3$)$_4$—4-SCH$_3$ | A | Cream solid | 2.23(3H,s); 2.39 (6H,s); 2.58(6H,s); 10.57(1H,s). |
| 2,3,4,6-(CH$_3$)$_4$—5-CH$_2$OCH$_3$ | C | Colourless solid; mp 55° C. | 2.24(3H,s); 2.38 (3H,s); 2.44(3H,s); 2.53(3H,s); 3.44 (3H,s); 4.51(2H,s); 10.65(1H,s). |
| 2,3,5,6-(CH$_3$)$_4$—4-SC$_4$H$_9$—n | A | Yellow oil | 0.71–1.83(9H,m); 2.43(6H,s); 2.57 (6H,s); 10.54(1H,s) |
| 2,4,6-(CH$_3$)$_3$—3-CH$_2$OCH$_3$ | C | Oil | 2.41(3H,s); 2.53 (3H,s); 2.62(3H,s); 3.44(3H,s); 4.51 (2H,s); 6.96(1H,s); 10.37(1H,s). |
| 2,4-(CH$_3$)$_2$—6-OCF$_2$H | B | Colourless oil | 2.34(3H,s); 2.54 (3H,s); 6.57(1H,t, J=80Hz); 6.83(2H, br.s); 10.43(1H,s). |
| 2,3,5,6-(CH$_3$)$_4$—4-OCH$_2$C$_6$H$_5$ | A | Yellow oil | 2.20(6H,s); 2.36 (6H,s); 4.68(2H,s); 7.32(5H,m); 10.56 (1H,s). |
| 2,6-(CH$_3$)$_2$—4-OCH$_2$C$_6$H$_5$ | A | Brown solid, mp 65° C. | Not recorded |
| 2,3,5,6-(CH$_3$)$_4$—4-OCH$_2$CH=CH$_2$ | A | Colourless oil, slowly solidified | 2.16(6H,s); 2.36 (6H,s); 4.16(2H,m); 5.28(2H,m); 5.84–6.28(1H,m); 10.52 (1H,s). |
| 2,6-(CH$_3$)$_2$ | C | Colourless solid, mp 31° C. | Not recorded |
| 2,4-(CH$_3$)$_2$—6 | A | Brown oil | 2.31(3H,s); 2.53 |

TABLE 2-continued

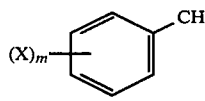

| (X)$_m$ | Method | Appearance | Proton Chemical Shift δ in ppm (CDCl$_3$) |
|---|---|---|---|
| OCH$_3$ | | | (3H,s); 3.84(3H,s); 6.49–6.63(2H,m); 10.56(1H,s). |
| 2,4,6-(CH$_3$)$_3$—3-SCH$_3$ | A | Brown oil | Not purified |
| 2,4-(CH$_3$)$_2$—6 | A | Yellow oil; | 2.30(3H,s); 2.50 |
| OCH$_2$C$_6$H$_5$ | | slowly solidified | (3H,s); 5.13(2H, s); 6.66(1H,s); 6.74(1H,s); 7.41 (5H,m); 10.67(1H, s). |
| 2,4,6-(CH$_3$)$_3$—3-OCF$_2$H | B | Oil | 2.30(3H,s); 2.51 (6H,s); 6.57(1H,t, J=80Hz); 6.83(2H, br.s); 10.43(1H,s). |

EXAMPLE 35

The 5-arylcyclohexane-1,3-diones of formula IX used in the preparation of the compounds of formula I were prepared from the appropriate benzaldehyde derivative following essentially the same procedure as that described in Example 1 part (ii).

The majority of the 5-arylcyclohexane-1,3-diones of formula IX were obtained as solids and were characterized by their nuclear magnetic resonance spectra. For convenience, proton nuclear magnetic resonance (pmr) spectroscopic data and/or melting point data is recorded in Table 3 below.

TABLE 3

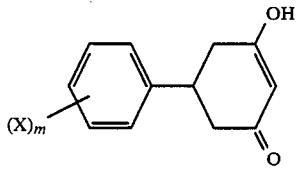

| (X)$_m$ | Appearance | Proton Chemical Shift δ in ppm (D$_6$-DMSO) |
|---|---|---|
| 2,4,6-(CH$_3$)$_3$—3-COCH$_3$ | Glassy solid | 2.20(3H,s); 2.24(3H,s); 2.38(3H,s); 2.45(3H,s); 2.45–3.40(4H,m); 3.90(1H, m); 5.25(1H,s); 6.85(1H, s); 11.0(1H,br.s). |
| 2,4,6-(CH$_3$)$_3$—3-COCH$_3$—5-C$_2$H$_5$ | Glassy solid | 1.02(3H,t); 2.18(3H,s); 2.20(3H,s); 2.38(3H,s); 2.42(3H,s); 2.42–3.00(6H, m); 3.90(1H,s); 5.30(1H, s); 11.9(1H,br.s). |
| 2,3,5,6-(CH$_3$)$_4$—4-COCH$_3$ | Yellow solid | 2.00(6H,s); 2.20(6H,s); 2.40(3H,s); 2.40–3.40(4H, m); 3.85(1H,m); 5.22(1H, s); 11.0(1H,br.s). |
| 2,3,4,6-(CH$_3$)$_4$—5-COCH$_3$ | Colourless solid, mp 100° C. | Not recorded |
| 3-Cl—6-OCF$_2$H—2,4-(CH$_3$)$_2$ | Pale yellow oil | 2.36(3H,s); 2.43(3H,s); 2.4–4.0(5H,m); 5.6(2H, br.s); 6.52(1H,t,J=82Hz); 6.82(1H,s). |
| 2,3,4,5-(CH$_3$)$_4$—6-SCH$_3$ | Light brown solid; mp 185° C. (decomp.) | Not recorded |
| 2,3,5,6-(CH$_3$)$_4$—4-SCH$_3$ | White solid, mp 225° C. | Not recorded |
| 2,3,4,6-(CH$_3$)$_4$—5-CH$_2$OCH$_3$ | Low melting point solid | 2.0–2.5(12H,m); 2.5–3.9 (5H,m); 3.47(3H,s); 4.48 (2H,s); 5.60(1H,s). |
| 2,3,5,6-(CH$_3$)$_4$—4-S(CH$_2$)$_3$CH$_3$ | White solid mp 190-195° C. | Not recorded |
| 2,4,6-(CH$_3$)$_3$—3-CH$_2$OCH$_3$ | Oil | Not recorded |
| 2,4-(CH$_3$)$_2$—6-OCF$_2$H | Light brown solid | 2.22(3H,s); 2.29(3H,s); 2.30–3.90(5H,m); 5.32(1H, s); 6.84(1H,s); 6.90(1H, s); 7.28(1H,t,J=82Hz). |
| 2,3,5,6-(CH$_3$)$_4$—4-OCH$_2$C$_6$H$_5$ | Yellow solid mp 186° C. | Not recorded |
| 2,6(CH$_3$)$_2$—4-OCH$_2$C$_6$H$_5$ | Brown solid mp 65° C. | Not recorded |
| 2,3,5,6-(CH$_3$)$_4$—4-OCH$_2$CH=CH$_2$ | Yellow solid mp 168° C. | Not recorded |
| 2,6-(CH$_3$)$_2$ | Orange solid | 2.00–3.80(11H,m); 5.28 (1H,s); 6.96(3H,m); 11.2 (1H,br.s). |
| 2,4-(CH$_3$)$_2$—6-OCH$_3$ | Cream solid mp 158° C. | Not recorded |
| 2,4,6-(CH$_3$)$_3$—3-OCF$_2$H | Pale brown solid | 2.23(3H,s); 2.30–4.00(5H, m); 2.32(3H,s); 2.35(3H, s); 5.62(1H,s); 6.22(1H, t,J=82Hz); 6.88(1H,s); 9.68(1H,br.s). |
| 2,4,6-(CH$_3$)$_3$—3-SCH$_3$ | Brown oil | Not recorded |
| 2,4-(CH$_3$)$_2$—6-OCH$_2$C$_6$H$_5$ | Yellow solid | 2.25(3H,s); 2.30(3H,s); 2.82–4.50(5H,m); 5.30(3H, s); 6.63(1H,s); 6.80(1H, s); 7.20–7.61(5H,m); 11.60(1H,s); (solvent D$_6$-acetone) |
| 2,4,6-(CH$_3$)$_3$ | Pale yellow solid mp 165° C. | 2.00–4.10(1H,m); 5.20(1H, s); 6.80(2H,s); 11.2(1H, br.s). |

EXAMPLE 36

The 2-acyl-5-arylcyclohexane-1,3-diones of formula XIII used in the preparation of the compounds of formula I were prepared from the corresponding 5-arylcyclohexane-1,3-diones of formula IX by acylation using the appropriate acyl derivative following essentially the same procedure as that described in Example 1 part (iii).

The majority of the 2-acyl-5-arylcyclohexane-1,3-diones of formula XIII were obtained as oils and were characterized by their nuclear magnetic resonance spectra. For convenience, proton nuclear magnetic resonance (pmr) spectroscopic data and/or melting point data is recorded in Table 4 below.

TABLE 4

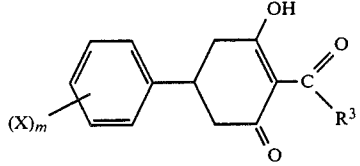

XIII

| $(X)_m$ | $R^3$ | Appearance | Proton Chemical Shift δ in ppm (CDCl$_3$) |
|---|---|---|---|
| 2,4,6-(CH$_3$)$_3$—3-NO$_2$ | C$_2$H$_5$ | Yellow solid; mp 174° C. | Not recorded |
| 2,4,6-(CH$_3$)$_3$—3,5(NO$_2$)$_2$ | C$_2$H$_5$ | Yellow solid; mp 252° C. | Not recorded |
| 4-CH$_3$—3,5-NO$_2$ | C$_2$H$_5$ | Orange solid | 1.15(3H,t); 2.56 (3H,s); 2.59-3.23 (6H,m); 3.29-3.80 (1H,m); 7.90(2H,s); 18.28(1H,s). |
| 2,4-(CH$_3$)$_2$—6-CH$_3$O—3,5-(NO$_2$)$_2$ | C$_2$H$_5$ | Orange solid | 1.21(3H,t); 2.18 (3H,s); 2.30 (3H,s); 2.41-3.79(7H,m); 3.87(3H,s); 18.36(1H,s). |
| 2,6-(CH$_3$)$_2$—3-SO$_2$N(CH$_3$)$_2$ | C$_2$H$_5$ | Orange solid; mp 169-170° C. | Not recorded |
| 2,4,6-(CH$_3$)$_3$—3-NO$_2$ | n-C$_3$H$_7$ | Orange oil; slowly solidified | 0.97(3H,t); 1.69 (2H,m); 2.20(3H,s); 2.26(3H,s); 2.40(3H,s); 2.45-4.00(7H,m); 6.86(1H,s); 18.24(1H,s). |
| 2,4,6-(CH$_3$)$_3$—3-NH$_2$ | n-C$_3$H$_7$ | Orange oil | 1.01(3H,t); 1.70(2H,m); 2.16(3H,s); 2.22(3H,s); 2.28(3H,s); 2.36-2.88(3H,m); 3.05(2H,t); 3.23-4.32(4H,m); 6.80(1H,s); 18.27(1H,br.s) |
| 2,4,6-(CH$_3$)$_3$—3-SOCH$_3$ | C$_2$H$_5$ | Brown oil | 1.17(3H,t); 2.39-4.06(7H,m); 2.40(3H,s); 2.54(3H,s); 2.65(3H,s); 2.86(3H,s); 6.88(1H,s); 18.20(1H,br.s). |
| 2,4,6-(CH$_3$)$_3$—3-SO$_2$CH$_3$ | C$_2$H$_5$ | Brown oil | 1.16(3H,t); 2.40-4.00(7H,m); 2.43(3H,s); 2.61(3H,s); 2.70(3H,s); 3.10(3H,s); 7.00(1H,s); 18.20(1H,br.s). |
| 2,4,6-(CH$_3$)$_3$—3-SO$_2$N(CH$_3$)$_2$ | C$_2$H$_5$ | Cream solid | 1.16(3H,s); 2.29-4.23(5H,m); 2.43(3H,s); 2.61(3H,s); 2.65(3H,s); 2.75(6H,s); 3.10(2H,q); 6.98(1H,s); 18.23(1H,s). |
| 2,4,6-(CH$_3$)$_3$—SO$_2$NH$_2$ | C$_2$H$_5$ | Cream solid | 1.17(3H,s); 2.71-4.16 (7H,m); 2.42(3H,s); 2.63(3H,s); 2.72(3H,s); 4.98(2H,s); 6.97(1H,s); 18.27(1H,s). |
| 2,4,6-(CH$_3$)$_3$—3-COCH$_3$ | C$_2$H$_5$ | Orange oil | 1.20(3H,t); 2.20(3H,s); 2.24(3H,s); 2.38(3H,s); 2.45(3H,s); 2.45-3.40(6H,m); 3.90(1H,m). |
| 2,4,6-(CH$_3$)$_3$—3-COC$_3$H$_7$—n | n-C$_3$H$_7$ | Yellow oil | 0.99(6H,t); 1.40-1.90(4H,m); 2.14(3H,s); 2.22(3H,s); 2.38(3H,s); 2.40-4.00(9H,m); 6.84(1H,s); 18.26(1H,s). |
| 2,4,6-(CH$_3$)$_3$—3-OCH$_3$—5-NO$_2$ | C$_2$H$_5$ | Orange oil | 1.15(3H,t); 2.01-3.91(19H,m); 6.61(1H,s); 6.90(1H,s); 18.22(1H,s). |
| 2,4,6-(CH$_3$)$_3$—3-Br—5-NO$_2$ | C$_2$H$_5$ | Brown oil | 1.15(3H,t); 2.20(3H,s); 2.30(3H,s); 2.40-3.40(6H,m); 2.60(3H,s); 4.00(1H,m); 18.40(1H,s). |
| 2,5,6-(CH$_3$)$_3$—3-CH$_2$NO$_2$ | C$_2$H$_5$ | Yellow oil | 1.15(3H,t); 2.27(3H,s); 2.30(3H,s); 2.31(3H,s); 2.50-3.40(1H,m); 4.00(1H,m); 5.43(2H,s); 7.01(1H,s); 18.20(1H,s). |
| 3,4,5-(CH$_3$)$_3$—2,6-(NO$_2$)$_2$ | C$_2$H$_5$ | Yellow oil | 1.14(3H,t); 2.22(6H,s); 2.33(3H,s); 2.64-3.18(6H,m); 18.22(1H,s). |
| 2,3,4,6-(CH$_3$)$_4$—5-NO$_2$ | C$_2$H$_5$ | Yellow oil | 1.19(3H,t); 2.16(3H,s); 2.20(6H,s); 2.32(3H,s); 2.32-3.40(6H,m); 3.90(1H,m); 18.20(1H,s). |
| 4-OH—3,5-(NO$_2$)$_2$ | C$_2$H$_5$ | Pale yellow | 1.12(3H,t); 2.4-3.8(7H,m); |

TABLE 4-continued

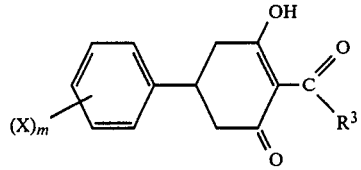

XIII

| (X)$_m$ | R$^3$ | Appearance | Proton Chemical Shift δ in ppm (CDCl$_3$) |
|---|---|---|---|
| | | solid | 8.18(2H,s); 11.00(1H,br.s); 18.16(1H,s). |
| 2,4,6-(CH$_3$)$_3$—3-COCH$_3$—5-C$_2$H$_5$ | C$_2$H$_5$ | Yellow oil | 1.00–1.25(6H,m); 2.18(3H,s); 2.20(3H,s); 2.38(3H,s); 2.42(3H,s); 2.42–3.40(8H,m); 3.90(1H,m); 18.25(1H,s). |
| 2,6-(CH$_3$)$_2$—3-NO$_2$ | C$_2$H$_5$ | Yellow oil; slowly solidified | 1.18(3H,t); 2.41–3.55(12H,m); 3.68–4.12(1H,m); 7.05(1H,d); 7.34(1H,d); 18.25(1H,s). |
| 2,3,5,6-(CH$_3$)$_4$—4-COCH$_3$ | C$_2$H$_5$ | Yellow oil | 1.15(3H,t); 2.00(6H,s); 2.20(6H,s); 2.40(3H,s); 2.40–3.40(6H,m); 3.85(1H,m); 18.25 (1H,s). |
| 2,4,6-(CH$_3$)$_3$—3-NHCOCH$_3$ | C$_2$H$_5$ | Orange solid | 1.18(3H,t); 2.01–3.91(19H,m); 6.61(1H,s); 6.90(1H,s); 18.22(1H,s). |
| 2,4,6-(CH$_3$)$_3$—3-CN | n-C$_3$H$_7$ | Pale yellow oil | 1.00(3H,t); 1.68(2H,m); 2.45(6H,s); 2.60(3H,s); 2.65–4.20(7H,m); 7.42(1H,s); 18.35(1H,s). |
| 2,3,4,6-(CH$_3$)$_4$—5-COCH$_3$ | C$_2$H$_5$ | Brown oil | 1.10(3H,t); 2.10–2.35(12H,m); 2.42(3H,s); 2.42–3.45(6H,m); 3.80(1H,m); 18.10(1H,s). |
| 2,4-(CH$_3$)$_2$—3-Cl—6-OCF$_2$H | C$_2$H$_5$ | Yellow oil | 1.20(3H,t); 2.35(3H,s); 2.40–4.00(7H,m); 2.43(3H,s); 6.54(1H,t,J=82Hz); 6.85(1H,s); 18.25(1H,s). |
| 2,3,4,5-(CH$_3$)$_4$—6-SCH$_3$ | C$_2$H$_5$ | Pale brown oil | 1.17(3H,t); 2.18(3H,s); 2.24(3H,s); 2.26(3H,s); 2.30–5.03(5H,m); 2.32(3H,s); 2.62(3H,s); 3.11(2H,q); 18.25(1H,s). |
| 2,3,5,6-(CH$_3$)$_4$—4-SCH$_3$ | C$_2$H$_5$ | Red-brown oil | 1.18(3H,t); 2.19(3H,s); 2.11–4.23(5H,m); 2.19(3H,s;) 2.32(6H,s); 2.60(6H,s); 3.11(2H,q); 18.23(1H,s). |
| 2,6-(CH$_3$)$_2$—4-OH | C$_2$H$_5$ | Yellow oil | 1.18(3H,t); 2.25(6H,s); 2.42–3.92(7H,m); 6.54(2H,s); 6.86(1H,br.s); 18.39(1H,s). |
| 2,3,4,5-(CH$_3$)$_4$—6-SCH$_3$ | n-C$_3$H$_7$ | Pale brown oil | 1.01(3H,t); 1.70(2H,m); 2.18(3H,s); 2.25(3H,s); 2.26(3H,s); 2.30–4.74(7H,m); 2.33(3H,s); 2.63(3H,s); 18.34(1H,s). |
| 2,3,5,6-(CH$_3$)$_4$—4-SCH$_3$ | n-C$_3$H$_7$ | Red oil | 1.02(3H,t); 1.71(2H,m); 2.19(3H,s); 2.30–4.23(7H,m); 2.33(6H,s); 2.60(6H,s); 18.30 (1H,s). |
| 2,6-(CH$_3$)$_2$—4-O$_2$CCH$_3$ | C$_2$H$_5$ | Cream solid | 1.15(3H,t); 2.28(3H,s); 2.39(6H,s); 2.48–3.98(7H,m); 6.74(2H,s); 18.30(1H,s). |
| 2,4,6-(CH$_3$)$_3$—3-COCH$_2$CH$_3$ | C$_2$H$_5$ | Brown oil | 1.00–1.40(6H,m); 2.12(3H,s); 2.20–3.80(9H,m); 2.22(3H,s); 2.39(3H,s); 6.83(1H,s); 18.16(1H,s). |
| 2,4-(CH$_3$)$_2$—6-OH | n-C$_3$H$_7$ | White solid | 1.01(3H,t); 1.76(2H,m); 2.22(3H,s); 2.28(3H,s); 2.30–2.42(2H,m); 3.05(2H,t); 3.28–4.03(3H,m); 6.14(1H,s); 6.48(1H,s); 6.57(1H,s); 18.47(1H,s). |
| 2,3,4,6-(CH$_3$)$_4$—5-CH$_2$OCH$_3$ | n-C$_3$H$_7$ | Yellow oil | 1.00(3H,t); 1.69(2H,m); 2.21(3H,s); 2.32(6H,s); 2.41(3H,s); 2.50–4.00(7H,m); 3.44(3H,s); 4.48(2H,s); 18.39(1H,s). |
| 2,3,5,6-(CH$_3$)$_4$—4-SC$_4$H$_9$—n | n-C$_3$H$_7$ | Pale yellow oil | 0.74–4.17(21H,m); 2.30(6H,s); 2.57(6H,s); 18.26 (1H,s). |
| 2,4,6-(CH$_3$)$_3$—3-CH$_2$OCH$_3$ | n-C$_3$H$_7$ | Yellow oil | 1.00(3H,t); 1.26(3H,t); 1.72(2H,m); 2.34(6H,s); 2.44(3H,s); 2.60–3.90(7H,m); |

TABLE 4-continued

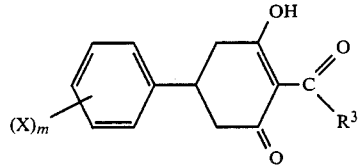

XIII

| $(X)_m$ | $R^3$ | Appearance | Proton Chemical Shift δ in ppm (CDCl$_3$) |
|---|---|---|---|
| 2,4-(CH$_3$)$_2$—6-OCF$_2$H | n-C$_3$H$_7$ | Yellow oil | 3.60 (2H,q); 4.50(2H,s); 6.92(1H,s); 18.39(1H,s). 1.00(3H,t); 1.60(2H,m); 2.27(3H,s); 2.30(3H,s); 2.30–3.80(7H,m); 6.52(1H,t,J=82Hz); 6.70(1H,s); 6.82(1H,s); 18.14(1H,s). |
| 2,4,6-(CH$_3$)$_3$—3-COCH$_3$ | n-C$_3$H$_7$ | Orange oil | 1.00(3H,t); 1.62(2H,m); 2.19(3H,s); 2.23(3H,s); 2.40(3H,s); 2.44(3H,s); 2.44–3.30(6H,m); 3.80(1H,m); 6.85(1H,s); 18.30(1H,s). |
| 2,3,5,6-(CH$_3$)$_4$—4-OCH$_2$C$_6$H$_5$ | n-C$_3$H$_7$ | Pale yellow solid; mp 102° C. | Not recorded |
| 2,6-(CH$_3$)$_2$—4-OCH$_2$C$_6$H$_5$ | C$_2$H$_5$ | Orange oil | 1.50(3H,t); 2.36(6H,s); 2.42–3.98(7H,m); 5.01(2H,s); 6.66(2H,s); 7.35(5H,m); 18.36(1H,s). |
| 2,4-(CH$_3$)$_2$—6-OCH$_2$C$_6$H$_5$ | C$_2$H$_5$ | Orange oil | 1.12(3H,t); 2.25–2.77(2H,m); 2.28(6H,s); 3.05(2H,q); 3.26–3.80(3H,m); 5.07(2H,s); 6.63(2H,s); 7.35(5H,m); 18.27(1H,s). |
| 2,4,6-(CH$_3$)$_3$—3-CH$_2$OH | n-C$_3$H$_7$ | Yellow oil | 1.00(3H,t); 1.69(2H,m); 2.37(6H,s); 2.47(3H,s); 2.58–4.00(7H,m); 4.73(2H,s); 5.5(1H,br.s); 6.92(1H,s); 18.39(1H,s). |
| 2,3,5,6-(CH$_3$)$_4$—4-OCH$_2$CH=CH$_2$ | n-C$_3$H$_7$ | Colourless oil | 1.00(3H,t); 1.60(2H,m); 2.16(6H,s); 2.24(6H,s); 2.40–4.00(5H,m); 3.04(2H,t); 4.16(2H,m); 5.28(2H,m); 6.00(1H,m); 18.24(1H,s). |
| 2,3,4,5-(CH$_3$)$_4$—6-SCH$_3$ | n-C$_3$H$_7$ | White solid; mp 132° C. | Not recorded |
| 2,4,6-(CH$_3$)$_3$—3-CH$_2$SC$_4$H$_9$—n | n-C$_3$H$_7$ | Yellow oil | 0.83–1.10(6H,m); 1.23–1.84(6H,m); 2.34(3H,s); 2.39(3H,s); 2.47(3H,s); 2.50–4.00(9H,m); 3.76(2H,s); 6.92(1H,s); 18.39 (1H,s). |
| 2,4,6-(CH$_3$)$_3$—3-OCF$_2$H | C$_2$H$_5$ | Yellow oil | 1.07(3H,t); 2.20–3.80(7H,m); 2.22(3H,s); 2.29(3H,s); 2.33(3H,s); 6.23(1H,t,J=82Hz); 6.86(1H,s); 18.17 (1H,s). |
| 2,6-(CH$_3$)$_2$ | C$_2$H$_5$ | Yellow oil | 1.20(3H,t); 2.40(6H,s); 2.40–4.00(7H,m); 7.00(3H,s); 18.10(1H,s). |
| 2,4,6-(CH$_3$)$_3$ | C$_2$H$_5$ | Solid; mp 86–88° C. | 1.60(3H,t,J=8Hz); 2.24(3H,s); 2.37(6H,s); 2.64–5.26(7H,m); 6.84(2H,m); 18.26(1H,s). |
| 2,4,6-(CH$_3$)$_3$ | n-C$_3$H$_7$ | Oil | 1.01(3H,t); 1.30–1.60(2H,m); 2.23(3H,s); 2.37(6H,s); 2.40–3.45(7H,m); 6.83(2H,s); 18.24(1H,s). |

EXAMPLE 37

The majority of the compounds of the invention were obtained as oils and were characterized by, and can be identified by, their nuclear magnetic resonance spectra. For convenience proton nuclear magnetic resonance (pmr) spectroscopic data and/or melting point data is recorded in Table 5 below.

TABLE 5

| Compound No | Appearance | Proton Chemical Shift δ in ppm (CDCl$_3$) |
|---|---|---|
| 1 | Pale yellow oil | 1.11–1.42(6H,m); 2.21(3H,s); 2.30(3H,s); 2.42(3H,s); 2.60–4.29(9H,m); 6.96(1H,s); 15.10 (1H,s). |
| 2 | White solid; mp 170° C. | 1.19(3H,t); 1.34(3H,t); 2.16 (3H,s); 2.35(6H,s); 2.3–4.2 (9H,m); 15.34(1H,s). |
| 3 | Pale orange solid; mp 100° C. | 1.15(3H,t); 1.35(3H,t); 2.55 (3H,s); 2.5–3.5(7H,m); 4.14 (2H,q); 7.93(2H,s); 15.3 (1H,bs). |
| 4 | Pale orange oil | 1.19(3H,t); 1.34(3H,t); 2.18 (3H,s); 2.32(3H,s); 2.3–3.8 (7H,m); 3.88(3H,s); 4.14(2H,q); 15.26(1H,bs). |
| 5 | Pale yellow oil | 1.20(3H,t); 1.34(3H,t); 2.49 (3H,s); 2.67(3H,s); 2.82(6H, s); 2.5–4.0(7H,m); 4.14(2H,q); 7.13(1H,d); 7.73(1H,d); 15.1 (1H,bs). |
| 6 | Pale orange oil | 1.00(3H,t); 1.33(3H,t); 1.5 (2H,m); 2.20(3H,s); 2.30(3H,s); 2.43(3H,s); 2.6–4.0(7H,m); 4.13(2H,q); 6.97(1H,s); 15.2 (1H,bs). |
| 7 | Pale brown oil | 1.00(3H,t); 1.5(2H,m); 2.21 (3H,s); 2.29(3H,s); 2.42(3H,s); 2.60–3.9(7H,m); 4.55(2H,d); 5.2–5.4(2H,m); 5.79–5.96(1H,m); 6.96(1H,s); 14.8(1H,bs). |
| 8 | Orange oil | 1.00(3H,t); 1.32(3H,t); 1.5 (2H,m); 2.14(3H,s); 2.22(3H,s); 2.30(3H,s); 2.4–3.9(7H,m); 4.12(2H,q); 6.78(1H,s). |
| 9 | Brown oil | 1.20(3H,t); 1.34(3H,t); 2.39 (3H,s); 2.53(3H,s); 2.64(3H,s); 2.78(3H,s); 2.5–4.0(7H,m); 4.13(2H,q); 6.85(1H,s); exchangeable proton not observed |
| 10 | Brown oil | 1.20(3H,t); 1.34(3H,t); 2.45 (3H,s); 2.64(3H,s); 2.74(3H,s); 3.11(3H,s); 2.5–4.1(7H,m); 4.14 (2H,q); 7.00(1H,s); exchangeable proton not observed. |
| 11 | Pale yellow oil, slowly solidifies | 1.20(3H,t); 1.34(3H,t); 2.42 (3H,s); 2.62(3H,s); 2.65(3H, s); 2.75(6H,s); 2.5–4.0(7H,m); 4.13(2H,q); 6.96(1H,s); 15.0 (1H,bs). |
| 12 | Pale yellow oil, slowly solidifies | 1.20(3H,t); 1.34(3H,t); 2.41 (3H,s); 2.61(3H,s); 2.72(3H, s); 2.5–4.0(7H,m); 4.13(2H,q); 5.00(2H,bs); 6.96(1H,s); 15.1 (1H,bs). |
| 13 | Pale yellow oil | 1.16(3H,t); 1.35(3H,t); 2.16 (3H,s); 2.27(3H,s); 2.39(3H,s); 2.45(3H,s); 2.45–3.5(7H,m); 4.14(2H,q); 6.87(1H,s); 15.04 (1H,bs). |
| 14 | Brown Oil | 1.00(6H,t); 1.34(3H,t); 1.5 (4H,m); 2.14(3H,s); 2.22(3H,s); 2.38(3H,s); 2.4–4.1(7H,m); 4.13(2H,q); 6.85(1H,s); 15.1 (1H,bs). |
| 15 | Pale yellow oil | 1.00(3H,t); 1.32(6H,t); 1.5 (2H,m); 2.30(3H,s); 2.38(6H,s); 2.4–4.3(11H,m); 6.90(1H,s); 8.28(1H,s); 15.10(1H,bs). |
| 16 | Orange oil | 1.20(3H,t); 1.34(3H,t); 2.18 (3H,s); 2.26(3H,s); 2.38(3H, s); 2.4–4.0(7H,m); 3.69(3H, s); 4.14(2H,q); 15.16(1H,bs). |
| 17 | Pale yellow oil | 1.13–1.42(6H,m); 2.25(3H,s); 2.34(3H,s); 2.59(3H,s); 2.5–3.9(7H,m); 4.14(2H,q); 15.62 (1H,bs). |
| 18 | Pale brown oil | 1.12–1.41(6H,m); 2.05–3.08(15H, m); 4.01–4.25(3H,m); 5.42(2H, s); 7.08(1H,s) 15.05(1H,bs). |
| 19 | Pale yellow oil | 1.16(3H,t); 1.34(3H,t); 2.21 (6H,s); 2.32(3H,s); 2.4–3.0 (7H,m); 4.10(2H,q); 15.4(1H,bs). |
| 20 | Brown oil | 1.11–1.41(6H,m); 2.15(3H,s); 2.24(6H,s); 2.36(3H,s); 2.4–3.9(7H,m); 4.14(2H,q); 15.10 (1H,bs). |
| 21 | Yellow oil | 1.15(3H,t); 1.34(3H,t); 2.5–3.7(7H,m); 4.12(2H,q); 8.18 (2H,s); exchangeable protons not observed. |
| 22 | Brown oil | 1.03–1.41(9H,m); 2.17(3H,s); 2.24(3H,s); 2.38(3H,s); 2.46 (3H,s); 2.5–3.9(9H,m); 4.14 (2H,q); 15.02(1H,bs). |
| 23 | Pale yellow oil | 1.20(3H,t); 1.34(3H,t); 2.47 (3H,s); 2.49(3H,s); 2.4–4.0 (7H,m); 4.14(2H,q); 7.13(1H,d); 7.49(1H,d); 15.19(1H,bs). |
| 24 | Brown oil | 1.12–1.42(6H,m); 2.11(6H,s); 2.29(6H,s); 2.46(3H,s); 2.5–3.9(7H,m); 4.15(2H,q); 15.05 (1H,bs). |
| 25 | Pale yellow oil | 1.19(3H,t); 1.33(3H,t); 2.16 (3H,s); 2.21(3H,s); 2.26(3H,s); 2.33(3H,s); 2.4–4.0(7H,m); 4.13 (2H,q); 6.92(1H,s); 7.26(1H,bs); 15.12(1H,bs). |
| 26 | Pale yellow oil | 1.00(3H,t); 1.34(3H,t); 1.5 (2H,m); 2.44(3H,s); 2.46(3H,s); 2.63(3H,s); 2.5–4.0(7H,m); 4.14(2H,q); 6.98(1H,s); 15.1 (1H,bs). |
| 27 | Brown oil | 1.19(3H,t); 1.34(3H,t); 2.14 (3H,s); 2.18(3H,s); 2.24(3H,s); 2.35(3H,s); 2.46(3H,s); 2.5–4.0(7H,m); 4.14(2H,q); 15.04 (1H,bs). |
| 28 | Pale brown oil | 1.20(3H,t); 1.33(3H,t); 2.37 (3H,s); 2.46(3H,s); 2.5–4.0 (7H,m); 4.13(2H,q); 6.54(1H,t, J=82Hz); 6.85(1H,s); 14.88 (1H,bs). |
| 29 | Yellow solid mp 122° C. | 1.21(3H,t); 1.41(3H,t); 2.18(3H, s); 2.25(6H,s); 2.34(3H,s); 2.45–3.95(7H,m); 2.62(3H,s); 4.13(2H, q); 14.95(1H,s). |
| 30 | Red brown oil | 1.20(3H,t); 1.34(3H,t); 2.18(3H, s); 2.31(6H,s); 2.40–3.89(7H,m); 2.57(6H,s); 4.09(2H,q); 14.96 (1H,s). |
| 31 | Cream solid | 1.09–1.38(6H,m 2.34(6H,s); 2.47–3.80(7H,m); 4.11(2H,q); 5.42(1H,s); 6.51(2H,s); 14.97 (1H,s). |
| 32 | Pale yellow solid, mp 88° C. | 1.01(3H,t); 1.33(3H,t); 1.63(2H, m); 2.17(3H,s); 2.23(3H,s); 2.24 (3H,s); 2.32(3H,s); 2.34–3.97 (7H,m); 2.60(3H,s); 4.09(2H,q); 14.91(1H,s). |
| 33 | Pale yellow oil | 1.01(3H,t); 1.33(3H,t); 1.60(2H, m); 2.18–3.95(7H,m); 2.19(3H,s); 2.33(6H,s); 2.60(6H,s); 4.13 (2H,q); 15.05(1H,s). |
| 34 | Cream solid | 1.11–1.41(6H,m); 2.16–3.96(16H, m); 4.12(2H,q); 6.74(2H,s); 15.06(1H,s). |
| 35 | Brown oil | 1.19(6H,t); 1.34(3H,t); 2.12(3H, s): 2.20–3.90(9H,m); 2.22(3H,s); 2.39(3H,s); 4.12(2H,q); 6.86 (1H,s); 15.04(1H,s). |
| 36 | Cream solid, mp 134° C. | 1.00(3H,t); 1.32(3H,t); 1.56(2H, m); 2.18(6H,s); 2.29(6H,s); 2.30–3.36(6H,m); 3.64–4.00(1H, m); 4.12(2H,q); 4.86(1H,s); 15.10(1H,s). |
| 37 | Cream solid | 1.04(3H,t); 1.33(3H,t); 1.64(2H, m); 2.19(3H,s); 2.25(3H,s); 2.27–3.63(7H,m); 4.10(2H,q); 6.52(2H,s); 6.94(1H,s); 15.28 (1H,s). |

TABLE 5-continued

| Compound No | Appearance | Proton Chemical Shift δ in ppm (CDCl$_3$) |
|---|---|---|
| 38 | Pale yellow oil | 1.00(3H,t); 1.32(3H,t); 1.61(2H, m); 2.19(3H,s); 2.32(6H,s); 2.41(3H,s); 2.50–3.20(7H,m); 3.44(3H,s); 4.12(2H,q); 4.47 (2H,s); 15.02(1H,s). |
| 39 | Colourless oil | 1.00(3H,t); 1.33(3H,t); 2.32 (6H,s); 2.59(6H,s); 0.85–4.25 (20H,m); 15.08(1H,s). |
| 40 | Colourless oil | 0.97(3H,t); 1.32(3H,t); 1.64 (2H,m); 2.33(3H,s); 2.36(3H,s); 2.41(3H,s); 2.58–3.96(7H,m); 3.44(3H,s); 4.12(2H,q); 4.44 (2H,s); 6.86(1H,s); 15.06(1H,s). |
| 41 | Colourless oil | 1.00(3H,t); 1.29(6H,2xt); 2.34(6H,s); 2.42(3H,s); 2.58–3.85(7H,m); 3.58(2H,q); 4.12(2H, q); 4.47(2H,s); 6.86(1H,s); 14.96(1H,s). |
| 42 | Pale yellow oil | 1.00(3H,t); 1.52(3H,t); 1.60(2H, m); 2.27(3H,s); 2.30(3H,s); 2.30–3.80(7H,m); 4.10(2H,q); 6.52(1H,t,J=82Hz); 6.70(1H,s); 6.82(1H,s); 15.17(1H,br.s). |
| 43 | Yellow oil | 1.00(3H,t); 1.33(3H,t); 1.57(2H, m); 2.17(3H,s); 2.27(3H,s); 2.39 (3H,s); 2.46(3H,s); 2.50–3.02 (6H,m); 3.80(1H,m); 4.12(2H,q); 6.87(1H,s); 15.19(1H,s). |
| 44 | Light brown solid mp >265° C. | Not recorded |
| 45 | Yellow oil | 1.02(3H,t); 1.67(2H,m); 2.05–3.95(7H,m); 2.18(3H,s); 2.24 (3H,s); 2.25(3H,s); 2.33(3H,s); 2.62(3H,s); 4.65(2H,s); 5.72(1H, d); 5.93(1H,d); 13.86(1H,br.s). |
| 46 | Light green solid, mp 150° C. dec. | Not recorded |
| 47 | Yellow oil | 0.92(3H,t); 1.10(3H,t); 1.49(2H, m); 2.20–3.60(7H,m); 2.21(6H,s); 2.24(3H,s); 2.39(3H,s); 2.61 (3H,s); 4.11(2H,q); 7.30–7.63 (3H,m); 7.90–8.10(2H,m). |
| 48 | White powder mp 114° C. | 1.01(3H,t); 1.32(3H,t); 1.60(2H, m); 2.24(6H,s); 2.29(6H,s); 2.30–4.00(7H,m); 4.12(2H,q); 4.70(2H, s); 7.43(5H,m); 15.08(1H,s). |
| 49 | Orange oil | 1.12–1.44(6H,m); 2.30–2.71(2H,m); 2.39(6H,s); 2.90(2H,q); 3.83–3.00(3H,m); 4.15(2H,q); 5.02(2H, s); 6.66(2H,s); 7.34(5H,m); 15.03(1H,s). |
| 50 | Orange oil | 1.09–1.38(6H,m); 2.13–2.62(2H, m); 2.25(3H,s); 2.30(3H,s); 2.93 (2H,q); 3.57(3H,m); 4.08(2H,q); 5.07(2H,s); 6.63(2H,s); 7.34 (5H,m); 14.81(1H,s). |
| 51 | Pale yellow oil | 1.00(3H,t); 1.33(3H,t); 1.61 (2H,m); 2.37(6H,s); 2.47(3H,s); 2.57–3.90(7H,m); 4.12(2H,q); 4.73(2H,s); 6.87(1H,s). |
| 52 | Cream solid mp 70° C. | 1.01(3H,t); 1.32(3H,t); 1.60(2H, m); 2.20(6H,s); 2.28(6H,s); 2.32–3.48(6H,m); 3.68–3.88(1H, m); 4.00–4.20(5H,m); 5.28(2H,s); 5.92(1H,m); 15.07(1H,s). |
| 53 | Light brown oil | 1.00(3H,t); 1.60(2H,m); 2.00–5.03(11H,m); 2.18(3H,s); 2.23 (6H,s); 2.33(3H,s); 2.61(3H,s); 14.15(1H,s). |
| 54 | Cream solid mp 198° C. dec. | Not recorded |
| 55 | Pale yellow oil | 0.86(3H,t); 1.04–1.33(5H,m); 2.18(3H,s); 2.26(3H,s); 2.39(3H, s); 2.47(6H,s); 2.60–3.60(3H,m); 3.94–4.16(3H,m); 6.88(1H,s); 7.57(4H,m). |
| 56 | Pale yellow oil | 0.98–1.60(8H,m); 2.16–2.46(12H, m); 2.50–3.48(5H,m); 3.85–4.17 (3H,m); 6.89(1H,s); 8.26(4H,m). |
| 57 | Colourless oil | 1.00(3H,t); 1.33(3H,t); 1.67(2H, m); 1.89–3.54(5H,m); 2.24(6H,s); 2.39(3H,s); 2.59(3H,s); 3.20(3H, s); 4.13(2H,q); 4.69(2H,m); 11.14(1H,s). |
| 58 | Pale yellow oil | 0.94(3H,t); 1.28(3H,t); 1.36–1.72(2H,m); 2.16(3H,s); 2.18 (3H,s); 2.23(3H,s); 2.25(3H,s); 2.35–2.61(4H,m); 2.35(3H,s); 2.61(3H,s); 3.02–3.92(3H,m); 4.15(2H,q). |
| 59 | Pale yellow oil | 0.83–1.09(6H,m); 1.32(3H,t); 1.21–1.81(6H,m); 2.35(3H,s); 2.37(3H,s); 2.47(3H,s); 2.50–3.40(7H,m); 3.74(9H,m); 4.12(2H, q); 6.84(1H,s); 13.3(1H,br.s). |
| 60 | Pale brown oil | 1.19(3H,t); 1.34(3H,t); 2.22 (3H,s); 2.30(3H,s); 2.33(3H,s); 2.20–4.00(7H,m); 4.11(2H,q); 6.25(1H,t,J=83Hz); 6.87(1H,s); 15.09(1H,s). |

EXAMPLE 38

This non-limiting Example illustrates the preparation of formulations of the compounds of the invention.

(a) Emulsifiable Concentrate

Compound No. 13 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No. 13 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

(c) Emulsifiable Concentrate

Compound No. 13 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction).

(d) Dispersible Powder

Compound No. 13 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Strength Concentrate

Compound No. 13 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No. 13 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing a surface active agent and/or oil, to give aqueous compositions of the required concentration which were used, as described in Examples 39 and 40, in the evaluation of the preemergence and post-emergence herbicidal activity of the compounds.

EXAMPLE 39

The pre-emergent herbicidal activity of the compounds of the invention formulated as described in Example 38 was assessed by the following procedure.

The seeds of the test species were sown in rows 2 cm deep in soil contained in seed boxes. The monocotyledonous plants and dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Table 6 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 6

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 0.25 | 0 | 3 | 5 | 3 | 0 | 0 | 0 | 0 |
| 1 | 1.0 | 0 | 5 | 5 | 5 | 0 | 0 | 0 | 0 |
| 2 | 0.5 | 1 | 5 | 5 | 5 | 0 | 0 | 0 | 0 |
| 2 | 2.0 | 4 | 5 | 5 | 5 | 0 | 0 | 0 | 0 |
| 4 | 0.25 | 0 | 0 | 5 | 4 | 0 | 0 | 0 | 0 |
| 4 | 1.0 | 0 | 5 | 5 | 5 | 0 | 0 | 0 | 0 |
| 5 | 0.125 | 0 | 1 | 4 | 4 | 0 | 0 | 0 | 0 |
| 5 | 0.5 | 3 | 5 | 5 | 5 | 0 | 0 | 0 | 0 |
| 7 | 0.25 | 0 | 0 | 5 | 5 | 0 | 0 | 0 | 0 |
| 7 | 1.0 | 0 | 5 | 5 | 5 | 0 | 0 | 0 | 0 |
| 8 | 0.25 | 0 | 2 | 5 | 5 | 0 | 0 | 0 | 0 |
| 8 | 1.0 | 4 | 5 | 5 | 5 | 0 | 0 | 0 | 0 |
| 9 | 0.25 | 5 | 5 | 5 | 5 | 0 | 0 | 0 | 0 |
| 9 | 1.0 | 5 | 5 | 5 | 5 | 0 | 0 | 0 | 0 |
| 10 | 0.25 | 0 | 0 | 5 | 5 | 0 | 0 | 0 | 0 |
| 10 | 1.0 | 4 | 5 | 5 | 5 | 0 | 0 | 0 | 0 |
| 13 | 0.25 | 5 | 5 | 5 | 5 | 0 | 0 | 0 | 0 |
| 13 | 1.0 | 5 | 5 | 5 | 5 | 0 | 0 | 0 | 0 |
| 15 | 0.25 | 0 | 5 | 5 | 5 | 0 | 0 | 0 | 0 |
| 15 | 1.0 | 0 | 5 | 5 | 5 | 0 | 0 | 0 | 0 |
| 16 | 0.25 | 1 | 3 | 5 | 5 | 0 | 0 | 0 | 0 |
| 16 | 1.0 | 4 | 4 | 5 | 5 | 0 | 0 | 0 | 0 |
| 17 | 1.0 | 0 | 0 | 5 | 4 | 0 | 0 | 0 | 0 |
| 18 | 0.25 | 1 | 5 | 5 | 1 | 0 | 0 | 0 | 0 |
| 18 | 1.0 | 4 | 5 | 5 | 5 | 0 | 0 | 0 | 0 |
| 19 | 1.0 | 0 | 0 | 3 | 5 | 0 | 0 | 0 | 0 |
| 20 | 0.25 | 0 | 0 | 5 | 4 | 0 | 0 | 0 | 0 |
| 20 | 1.0 | 3 | 5 | 5 | 5 | 0 | 0 | 0 | 0 |
| 22 | 0.5 | 4 | 4 | 5 | 5 | 0 | 0 | 0 | 0 |
| 23 | 0.5 | 0 | 2 | 4 | 5 | 0 | 0 | 0 | 0 |
| 26 | 0.5 | 1 | 3 | 5 | 5 | 0 | 0 | 0 | 0 |
| 27 | 0.25 | 4 | 5 | 5 | 5 | 0 | 0 | 0 | 0 |
| 27 | 0.5 | 5 | 5 | 5 | 5 | 0 | 0 | 0 | 0 |
| 29 | 0.25 | 0 | 0 | 0 | 5 | 0 | 0 | 0 | 0 |
| 30 | 0.25 | 0 | 0 | 3 | 5 | 0 | 0 | 0 | 0 |
| 32 | 0.25 | 0 | 1 | 5 | 5 | 0 | 0 | 0 | 0 |
| 32 | 1.0 | 0 | 2 | 5 | 5 | 0 | 0 | 0 | 0 |
| 33 | 0.25 | 0 | 0 | 4 | 4 | 0 | 0 | 0 | 0 |
| 33 | 1.0 | 2 | 5 | 5 | 5 | 0 | 0 | 0 | 0 |
| 35 | 0.0625 | 3 | 5 | 5 | 5 | 0 | 0 | 0 | 0 |
| 35 | 0.25 | 5 | 5 | 5 | 5 | 0 | 0 | 0 | 0 |
| 35 | 1.0 | 5 | 5 | 5 | 5 | 0 | 0 | 0 | 0 |
| 36 | 1.0 | 0 | 3 | 4 | 4 | 0 | 0 | 0 | 0 |
| 38 | 0.25 | 0 | 4 | 4 | 5 | 0 | 0 | 0 | 0 |
| 38 | 1.0 | 4 | 5 | 5 | 5 | 0 | 0 | 0 | 0 |
| 39 | 0.25 | 0 | 0 | 2 | 5 | 0 | 0 | 0 | 0 |
| 39 | 1.0 | 0 | 2 | 5 | 5 | 0 | 0 | 0 | 0 |
| 40 | 0.25 | 0 | 4 | 2 | 4 | 0 | 0 | 0 | 0 |
| 40 | 1.0 | 1 | 5 | 5 | 5 | 0 | 0 | 0 | 0 |
| 41 | 0.25 | 1 | 3 | 3 | 5 | 0 | 0 | 0 | 0 |
| 41 | 1.0 | 3 | 3 | 4 | 3 | 0 | 0 | 0 | 0 |
| 42 | 0.25 | 0 | 0 | 0 | 4 | 0 | 0 | 0 | 0 |
| 42 | 1.0 | 4 | 4 | 5 | 5 | 0 | 0 | 0 | 0 |
| 48 | 1.0 | 1 | 4 | 4 | 5 | 0 | 0 | 0 | 0 |
| 52 | 1.0 | 3 | 2 | 4 | 5 | 0 | 0 | 0 | 0 |
| 60 | 0.25 | 0 | 0 | 4 | 5 | 0 | 0 | 0 | 0 |

EXAMPLE 40

The post-emergent herbicidal activity of the compounds of the invention formulated as described in Example 38 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glasshouse for a further 3 weeks and the effect of treatment was visually assessed by comparison with the untreated controls. The results are presented in Table 7 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 7

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 0.25 | 1 | 5 | 5 | 5 | 0 | 0 | 0 | 0 |
| 1 | 1.0 | 3 | 5 | 5 | 5 | 0 | 0 | 0 | 0 |
| 2 | 0.25 | 3 | 5 | 5 | 5 | 0 | 0 | 0 | 0 |
| 2 | 2.0 | 5 | 5 | 5 | 5 | 0 | 0 | 0 | 0 |
| 3 | 1.0 | 0 | 4 | 5 | 5 | 0 | 0 | 0 | 0 |
| 3 | 5.0 | 2 | 5 | 5 | 5 | 0 | 0 | 0 | 0 |
| 4 | 0.25 | 0 | 5 | 5 | 5 | 0 | 0 | 0 | 0 |
| 4 | 1.0 | 3 | 5 | 5 | 5 | 0 | 0 | 0 | 0 |
| 5 | 0.125 | 4 | 5 | 5 | 5 | 0 | 0 | 0 | 0 |
| 5 | 0.5 | 5 | 5 | 5 | 5 | 0 | 0 | 0 | 0 |
| 6 | 0.25 | 0 | 4 | 5 | 5 | 0 | 0 | 0 | 0 |
| 6 | 1.0 | 3 | 5 | 5 | 5 | 0 | 0 | 0 | 0 |
| 7 | 0.25 | 0 | 3 | 5 | 4 | 0 | 0 | 0 | 0 |
| 7 | 1.0 | 1 | 5 | 5 | 5 | 0 | 0 | 0 | 0 |
| 8 | 0.25 | 4 | 5 | 5 | 5 | 0 | 0 | 0 | 0 |
| 8 | 1.0 | 5 | 5 | 5 | 5 | 0 | 0 | 0 | 0 |
| 9 | 0.25 | 4 | 5 | 5 | 5 | 0 | 0 | 0 | 0 |
| 9 | 1.0 | 5 | 5 | 5 | 5 | 0 | 0 | 0 | 0 |
| 10 | 0.25 | 3 | 5 | 5 | 5 | 0 | 0 | 0 | 0 |
| 10 | 1.0 | 4 | 5 | 5 | 5 | 0 | 0 | 0 | 0 |
| 13 | 0.25 | 5 | 5 | 5 | 5 | 0 | 0 | 0 | 0 |
| 13 | 1.0 | 5 | 5 | 5 | 5 | 0 | 0 | 0 | 0 |
| 14 | 0.0625 | 3 | 5 | 5 | 5 | 0 | 0 | 0 | 0 |
| 14 | 0.50 | 5 | 5 | 5 | 5 | 0 | 0 | 0 | 0 |
| 15 | 0.25 | 2 | 5 | 5 | 5 | 0 | 0 | 0 | 0 |
| 15 | 1.0 | 5 | 5 | 5 | 5 | 0 | 0 | 0 | 0 |
| 16 | 0.25 | 3 | 5 | 5 | 5 | 0 | 0 | 0 | 0 |
| 16 | 1.0 | 5 | 5 | 5 | 5 | 0 | 0 | 0 | 0 |
| 17 | 0.25 | 1 | 5 | 5 | 5 | 0 | 0 | 0 | 0 |
| 17 | 1.0 | 3 | 5 | 5 | 5 | 0 | 0 | 0 | 0 |
| 18 | 0.25 | 2 | 5 | 5 | 5 | 0 | 0 | 0 | 0 |
| 18 | 1.0 | 5 | 5 | 5 | 5 | 0 | 0 | 0 | 0 |
| 20 | 0.25 | 3 | 5 | 5 | 5 | 0 | 0 | 0 | 0 |
| 20 | 1.0 | 4 | 5 | 5 | 5 | 0 | 0 | 0 | 0 |
| 22 | 0.5 | 5 | 5 | 5 | 5 | 0 | 0 | 0 | 0 |
| 23 | 0.5 | 2 | 5 | 5 | 5 | 0 | 0 | 0 | 0 |
| 24 | 0.5 | 5 | 5 | 5 | 5 | 0 | 0 | 0 | 0 |
| 26 | 0.5 | 4 | 5 | 5 | 5 | 0 | 0 | 0 | 0 |
| 27 | 0.5 | 5 | 5 | 5 | 5 | 0 | 0 | 0 | 0 |
| 29 | 0.25 | 0 | 4 | 4 | 4 | 0 | 0 | 0 | 0 |
| 30 | 0.25 | 3 | 5 | 5 | 5 | 0 | 0 | 0 | 0 |
| 32 | 0.25 | 0 | 5 | 4 | 4 | 0 | 0 | 0 | 0 |
| 32 | 1.0 | 3 | 5 | 5 | 5 | 0 | 0 | 0 | 0 |
| 33 | 0.25 | 1 | 5 | 5 | 5 | 0 | 0 | 0 | 0 |
| 33 | 1.0 | 5 | 5 | 5 | 5 | 0 | 0 | 0 | 0 |
| 35 | 0.0625 | 5 | 5 | 5 | 5 | 0 | 0 | 0 | 0 |
| 35 | 0.25 | 5 | 5 | 5 | 5 | 0 | 0 | 0 | 0 |
| 35 | 1.0 | 5 | 5 | 5 | 5 | 0 | 0 | 0 | 0 |
| 36 | 1.0 | 3 | 3 | 5 | 5 | 0 | 0 | 0 | 0 |
| 38 | 0.25 | 4 | 4 | 4 | 5 | 0 | 0 | 0 | 0 |
| 38 | 1.0 | 5 | 5 | 5 | 5 | 0 | 0 | 0 | 0 |
| 39 | 0.25 | 0 | 5 | 2 | 5 | 0 | 0 | 0 | 0 |

TABLE 7-continued

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 39 | 1.0 | 5 | 5 | 5 | 5 | 0 | 0 | 0 | 0 |
| 40 | 0.0625 | 0 | 5 | 5 | 5 | 0 | 0 | 0 | 0 |
| 40 | 0.25 | 5 | 5 | 5 | 5 | 0 | 0 | 0 | 0 |
| 40 | 1.0 | 5 | 5 | 5 | 5 | 0 | 0 | 0 | 0 |
| 41 | 0.0625 | 0 | 5 | 5 | 5 | 0 | 0 | 0 | 0 |
| 41 | 0.25 | 4 | 5 | 5 | 5 | 0 | 0 | 0 | 0 |
| 41 | 1.0 | 5 | 5 | 5 | 5 | 0 | 0 | 0 | 0 |
| 42 | 0.25 | 0 | 5 | 4 | 5 | 0 | 0 | 0 | 0 |
| 42 | 1.0 | 4 | 5 | 4 | 5 | 0 | 0 | 0 | 0 |
| 48 | 1.0 | 0 | 5 | 5 | 5 | 0 | 0 | 0 | 0 |
| 52 | 0.25 | 2 | 5 | 3 | 5 | 0 | 0 | 0 | 0 |
| 52 | 1.0 | 5 | 5 | 5 | 5 | 0 | 0 | 0 | 0 |
| 60 | 0.25 | 0 | 2 | 5 | 5 | 0 | 0 | 0 | 0 |

EXAMPLE 41

The compounds were formulated for test by mixing an appropriate amount with 5 ml of an emulsion prepared by diluting 160 ml of a solution containing 21.9 g per liter of "Span" 80 and 78.2 per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 8 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 8 below. A dash (-) means that no experiment was carried out.

The names of the test plants were as follows:
Sb: Sugar beet
Rp: Rape
Ct: Cotton
Sy: Soy bean
Mz: Maize
Ww: Winter wheat
Rc: Rice
Sn: *Senecio vulgaris*
Ip: *Ipomea purpurea*
Am: *Amaranthus retroflexus*
Pi: *Polygonum aviculare*
Ca: *Chenopodium album*
Ga: *Galium aparine*
Xa: *Xanthium pensylvanicum*
Ab: *Abutilon theophrasti*
Co: *Cassia obtusifolia*
Av: *Avena fatua*
Dg: *Digitaria sanguinalis*
Al: *Alopecurus myosuroides*
St: *Setaria viridis*
Ec: *Echinochloa crus-galli*

Sh: *Sorghum halepense*
Ag: *Agropyron repens*
Cn: *Cyperus rotundas*

Mz: Maize
Rc: Rice
Sy: Soyabean

TABLE 8

| Compound No | APPLICATION Method | Rate (kg/ha) | TEST PLANT |||||||||||
|---|---|---|---|---|---|---|---|---|---|---|---|---|---|
| | | | Sb | Rp | Ct | Sy | Mz | Ww | Rc | Sn | Ip | Am | Pi | Ca |
| 13 | PRE | 0.05 | — | — | — | — | 5 | 5 | 5 | — | — | — | — | — |
| 13 | POST | 0.025 | — | — | — | — | 5 | 4 | 4 | — | — | — | — | — |
| 22 | PRE | 0.05 | — | — | — | — | 5 | 5 | 5 | — | — | — | — | — |
| 22 | POST | 0.05 | — | — | — | — | 5 | 4 | 4 | — | — | — | — | — |
| 24 | PRE | 0.05 | — | — | — | — | 3 | 3 | 5 | — | — | — | — | — |
| 24 | POST | 0.025 | — | — | — | — | 2 | 2 | 1 | — | — | — | — | — |
| 27 | PRE | 0.05 | — | — | — | — | 4 | 5 | 4 | — | — | — | — | — |
| 27 | POST | 0.05 | — | — | — | — | 5 | 4 | 4 | — | — | — | — | — |
| 29 | PRE | 0.05 | — | — | — | — | 0 | 0 | 5 | — | — | — | — | — |
| 29 | POST | 0.05 | — | — | — | — | 2 | 1 | 4 | — | — | — | — | — |
| 30 | POST | 0.05 | — | — | — | — | 4 | 3 | 4 | — | — | — | — | — |

| Compound No | APPLICATION Method | Rate (kg/ha) | TEST PLANT |||||||||||
|---|---|---|---|---|---|---|---|---|---|---|---|---|---|
| | | | Ga | Xa | Ab | Co | Av | Dg | Al | St | Ec | Sh | Ag | Cn |
| 13 | PRE | 0.05 | — | — | — | — | 5 | 4 | 5 | 5 | 5 | 5 | — | — |
| 13 | POST | 0.025 | — | — | — | — | 4 | 4 | 4 | 5 | 4 | 3 | — | — |
| 22 | PRE | 0.05 | — | — | — | — | 5 | 5 | 5 | 5 | 5 | 4 | 5 | — |
| 22 | POST | 0.05 | — | — | — | — | 5 | 5 | 5 | 5 | 5 | 4 | 4 | — |
| 24 | PRE | 0.05 | — | — | — | — | 3 | 4 | 5 | 5 | 5 | 1 | 5 | — |
| 24 | POST | 0.025 | — | — | — | — | 4 | 4 | 4 | 4 | 5 | 4 | 2 | — |
| 27 | PRE | 0.05 | — | — | — | — | 5 | 5 | 5 | 5 | 5 | 3 | 5 | — |
| 27 | POST | 0.05 | — | — | — | — | 5 | 5 | 5 | 5 | 5 | 5 | 5 | — |
| 29 | PRE | 0.05 | — | — | — | — | 3 | 2 | 2 | 3 | 2 | 1 | 3 | — |
| 29 | POST | 0.05 | — | — | — | — | 4 | 3 | 4 | 4 | 4 | 0 | 0 | — |
| 30 | POST | 0.05 | — | — | — | — | 4 | 3 | 4 | 4 | 5 | 4 | 2 | — |

EXAMPLE 42

This Example illustrates the selective herbicidal activity of compounds of the invention.

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Tables 9 and 10 below. Damage to test plants was assessed afer 26 days on a scale of 0 to 9 where 0 is 0 to 10% damage and 9 is complete kill. The degree of herbicidal damage was assessed by comparison with untreated control plants and the results are given in Tables 9 and 10 below. A dash (-) means that no experiment was carried out.

The names of the test plants were as follows:

Ct: Cotton
Sg: Sorghum
Ec: *Echinochloa crus-gali*
Dg: *Digitaria sanguinalis*
St: *Setaria viridis*
Sh: *Sorghum halepense*
Pm: *Panicum maximum*
Sf: *Setaria faberii*
Ei: *Eleusine indica*

TABLE 9

| | POST-EMERGENCE HERBICIDAL ACTIVITY |||||||||||||
|---|---|---|---|---|---|---|---|---|---|---|---|---|---|
| Compound No | APPLICATION Rate (kg/ha) | TEST PLANT |||||||||||
| | | Mz | Rc | Sy | Ct | Sg | Ec | Dg | St | Sh | Pm | Sf | Ei |
| 5 | 0.20 | 9 | 9 | 0 | — | 9 | 9 | 9 | 9 | 9 | 9 | 9 | 9 |
| 5 | 0.025 | 6 | 3 | — | — | 7 | 9 | 9 | 8 | 9 | 9 | 9 | 9 |
| 13 | 0.16 | 9 | 9 | 0 | 0 | 9 | — | — | — | — | — | — | — |
| 13 | 0.04 | 9 | 8 | 0 | — | 9 | 9 | 9 | 9 | 9 | 9 | 9 | 9 |
| 13 | 0.02 | 9 | 9 | 0 | — | 9 | 9 | 9 | 8 | 9 | 9 | 9 | 9 |
| 22 | 0.20 | 9 | 9 | 0 | — | 9 | 9 | 9 | 9 | 9 | 9 | 9 | 9 |
| 22 | 0.025 | 7 | 1 | — | — | 9 | 9 | 9 | 9 | 6 | 7 | 7 | 9 |
| 27 | 0.20 | 9 | 9 | 0 | — | 9 | 9 | 9 | 9 | 9 | 9 | 9 | 9 |
| 27 | 0.025 | 9 | 8 | — | — | 8 | 9 | 9 | 8 | 8 | 9 | 8 | 9 |

TABLE 10

| | POST-EMERGENCE HERBICIDAL ACTIVITY ||||||||| 
|---|---|---|---|---|---|---|---|---|---|
| Compound No | APPLICATION Rate (kg/ha) | TEST PLANT ||||||||
| | | Ww | Br | Av | Al | Bs | Ll | St | Ap |
| 5 | 0.40 | 9 | 9 | 9 | 9 | — | — | 9 | — |
| 5 | 0.05 | 2 | 8 | 9 | 9 | — | — | 8 | — |
| 13 | 0.02 | 9 | 9 | 9 | 9 | 8 | 9 | 9 | 9 |
| 13 | 0.01 | 8 | 9 | 9 | 9 | 8 | 8 | 9 | 9 |
| 22 | 0.06 | 9 | — | 9 | 9 | 8 | 8 | 9 | 9 |
| 22 | 0.04 | — | — | 9 | 9 | 9 | 8 | 9 | 9 |
| 27 | 0.06 | 9 | — | 9 | 9 | 9 | 9 | 9 | 9 |
| 27 | 0.02 | — | — | 9 | 9 | 8 | 9 | 9 | 9 |

The names of the test plants were as follows:

Ww: Winter wheat
Br: Spring barley
Av: *Avena fatua*
Al: *Alopecurus myosuroides*
Bs: *Bromus sterilis*
Ll: *Lolium parenne*
Ap: *Apera spica venti*
St: *Setaria viridis*

We claim:

1. A compound of formula I

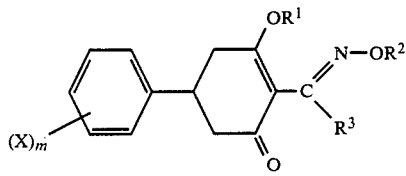

wherein:
X, which may be the same or different, are selected from the group consisting of: halogen; nitro; cyano; $C_1$ to $C_4$ alkyl; $C_1$ to $C_4$ alkoxy; $C_1$ to $C_4$ alkylsulfinyl; $C_1$ to $C_4$ alkylsulfonyl; $C_2$ to $C_6$ alkanoyl; sulfamoyl; N-($C_1$ to $C_6$ alkyl)sulfamoyl; N,N-di($C_1$ to $C_6$ alkyl)sulfamoyl; $C_1$ to $C_4$ alkyl substituted with $C_1$ to $C_4$ alkoxy; ($C_1$ to $C_6$ alkoxy)carbonyl; amino; $C_2$ to $C_4$ alkanoylamino and at least two of X are methyl and at least one of X is not selected from the group consisting of halogen, $C_1$ to $C_4$ alkyl, $C_1$ to $C_4$ alkoxy and nitro;

$R^1$ is selected from the group consisting of: hydrogen; $C_2$ to $C_6$ alkanoyl; benzoyl; substituted benzoyl wherein the benzene ring is substituted with from one to three substituents selected from the group consisting of halogen, nitro, $C_1$ to $C_6$ alkyl and $C_1$ to $C_6$ alkoxy; and an inorganic or organic cation selected from the alkali metal ions, the alkaline earth metal ions, the transition metal ions, the ammonium ion, and the tri- and tetra-(alkyl)ammonium ions wherein alkyl is selected from $C_1$ to $C_6$ alkyl and $C_1$ to $C_6$ hydroxyalkyl;

$R^2$ is selected from the group consisting of: $C_1$ to $C_6$ alkyl; $C_2$ to $C_6$ alkenyl; $C_2$ to $C_6$ alkynyl; $C_1$ to $C_6$ haloalky; $C_2$ to $C_6$ haloalkenyl; and $C_2$ to $C_6$ haloalkynyl;

$R^3$ is selected from $C_1$ to $C_6$ alkyl; and
m is an integer selected from 3 to 5.

2. A compound according to claim 1 wherein:
X, which may be the same or different, are selected from the group consisting of: halogen; nitro; cyano; $C_1$ to $C_4$ alkyl; $C_1$ to $C_4$ alkoxy; $C_1$ to $C_4$ alkylsulfinyl; $C_1$ to $C_4$ alkylsulfonyl; $C_2$ to $C_6$ alkanoyl; sulfamoyl; N,N-di($C_1$ to $C_6$ alkyl)sulfamoyl; $C_1$ to $C_4$ alkyl substituted with $C_1$ to $C_4$ alkoxy; amino; $C_2$ to $C_4$ alkanoylamino and at least two of X are methyl and at least one of X is not selected from the group consisting of halogen, $C_1$ to $C_4$ alkyl, $C_1$ to $C_4$ alkoxy and nitro;

$R^1$ is selected from the group consisting of: hydrogen, benzoyl; substituted benzoyl wherein the benzene ring is substituted with from one to three substituents selected from the group consisting of halogen, nitro, $C_1$ to $C_6$ alkyl and $C_1$ to $C_6$ alkoxy; and the alkali metal ions;

$R^2$ is selected from the group consisting of: $C_1$ to $C_6$ alkyl; $C_2$ to $C_6$ alkenyl and $C_2$ to $C_6$ alkynyl;

$R^3$ is selected from $C_1$ to $C_6$ alkyl; and
m is an integer selected from 3 to 5.

3. A compound according to claim 1 of formula

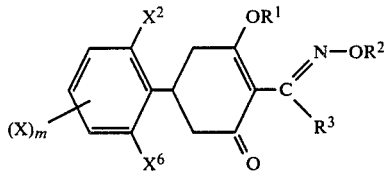

wherein:
X, $X^2$ and $X^6$ are independently selected from the group consisting of halogen, nitro, cyano, amino, methyl, ethyl, methoxy, methoxymethyl, ethoxymethyl, methylsulfinyl, methylsulfonyl, acetyl, butyryl, propionyl, sulfamoyl, N,N-dimethylsulfamoyl, and acetylamino, and at least one of X, $X^2$ and $X^6$ is not selected from the group consisting of halogen, methyl, ethyl, methoxy and nitro;

$R^1$ is selected from the group consisting of hydrogen, acetyl, benzoyl, nitrobenzoyl, and the cations of the alkali metals;

$R^2$ is selected from the group consisting of $C_1$ to $C_3$ alkyl, 2-haloethyl, allyl and 2-haloallyl;

$R^3$ is selected from $C_1$ to $C_3$ alkyl; and
m is an integer selected from 1 to 3.

4. A compound according to claim 3 of formula

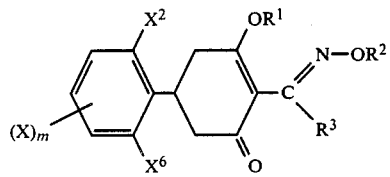

wherein:
X, $X^2$ and $X^6$ are independently selected from the group consisting of halogen, nitro, cyano, amino, methyl, ethyl, methoxy, methoxymethyl, ethoxymethyl, methylsulfinyl, methylsulfonyl, acetyl, butyryl, propionyl, sulfamoyl, N,N-dimethylsulfamoyl, and acetylamino, and at least two of X, $X^2$ and $X^6$ are methyl and at least one of X, $X^2$ and $X^6$ is not selected from the group consisting of halogen, methyl, ethyl, methoxy and nitro;

$R^1$ is selected from the group consisting of hydrogen, benzoyl, nitrobenzoyl and the cations of the alkali metals;

$R^2$ is selected from the group consisting of $C_1$ to $C_3$ alkyl and allyl;

$R^3$ is selected from $C_1$ to $C_3$ alkyl; and
m is an integer selected from 1 to 3.

5. A compound according to claim 3 or claim 4 wherein $X^2$ and $X^6$ are independently selected from halogen, methyl and methoxy.

6. A compound according to claim 3 of formula

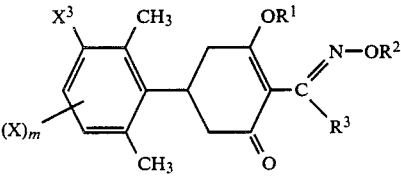

wherein:
- X and $X^3$ are independently selected from the group consisting of halogen, methyl, ethyl, methoxy, methoxymethyl, ethoxymethyl, methylsulfinyl, methylsulfonyl, acetyl, propionyl, sulfamoyl, and N,N-di(methyl)sulfamoyl, and at least one of X and $X^3$ is not selected from the group consisting of halogen, methyl, ethyl, methoxy and nitro;
- $R^1$ is selected from the group consisting of hydrogen, acetyl, benzoyl, nitrobenzoyl, and the cations of the alkali metals;
- $R^2$ is selected from the group consisting of $C_1$ to $C_3$ alkyl, 2-haloethyl, allyl and 2-haloallyl;
- $R^3$ is selected from $C_1$ to $C_3$ alkyl; and
- m is 0 or an integer selected from 1 and 2.

7. A compound according to claim 6 of formula

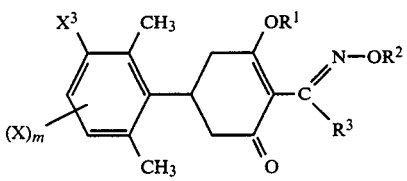

wherein:
- X and $X^3$ are independently selected from the group consisting of halogen, methyl, ethyl, methoxy, methoxymethyl, ethoxymethyl, methylsulfinyl, methylsulfonyl, acetyl, propionyl, sulfamoyl, and N,N-dimethylsulfamoyl, and at least one of X and $X^3$ is not selected from the group consisting of halogen, methyl, ethyl, methoxy and nitro;
- $R^1$ is selected from the group consisting of hydrogen, benzoyl, nitrobenzoyl and the cations of the alkali metals;
- $R^2$ is selected from the group consisting of $C_1$ to $C_3$ alkyl and allyl;
- $R^3$ is selected from $C_1$ to $C_3$ alkyl; and
- m is 0 or an integer selected from 1 and 2.

8. A compound according to claim 7 of formula

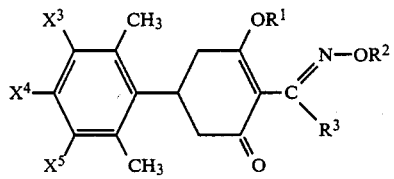

wherein:
- $X^3$ is selected from the group consisting of methoxymethyl, ethoxymethyl, methylsulfinyl, methylsulfonyl, acetyl, propionyl, sulfamoyl and N,N-di(methyl)sulfamoyl;
- $X^4$ is selected from hydrogen and methyl;
- $X^5$ is selected from hydrogen, methyl and ethyl;
- $R^1$ is selected from hydrogen, sodium and potassium;
- $R^2$ is selected from ethyl and allyl; and
- $R^3$ is selected from ethyl and n-propyl.

9. A compound according to claim 1 of formula

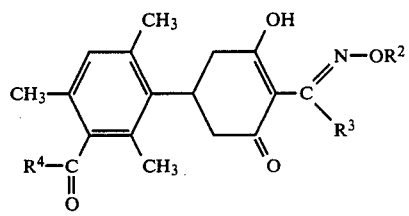

wherein:
- $R^2$ is selected from $C_1$ to $C_3$ alkyl, 2-haloethyl, allyl, 3-chloro allyl and $C_3$ to $C_4$ alkynyl;
- $R^3$ is selected from $C_1$ to $C_4$ alkyl;
- $R^4$ is selected from $C_1$ to $C_4$ alkyl.

10. A compound selected from the group consisting of:
- 2-[1-(ethoxyimino)propyl]-3-hydroxy-5-[2,6-dimethyl-3-(N,N-dimethylsulfamoyl)phenyl]cyclohex-2-en-1-one;
- 2-[1-(ethoxyimino)propyl]-3-hydroxy-5-[2,4,6-trimethyl-3-(N,N-dimethylsulfamoyl)phenyl]cyclohex-2-en-1-one;
- 2-[1-(ethoxyimino)propyl]-3-hydroxy-5-(2,4,6-trimethyl-3-sulfamoylphenyl)cyclohex-2-en-1-one;
- 5-(3-acetyl-2,4,6-trimethylphenyl)-2-[1-(ethoxyimino)propyl]-3-hydroxycyclohex-2-en-1-one;
- 5-(3-acetyl-5-ethyl-2,4,6-trimethylphenyl)-2-[1-(ethoxyimino)propyl]-3-hydroxycyclohex-2-en-1-en-1-one;
- 5-(3-acetyl-2,4,5,6-tetramethylphenyl)-2-[1-ethoxyimino)propyl]-3-hydroxycyclohex-2-en-1-one; and
- 5-(3-acetyl-2,4,6-trimethylphenyl)-2-[1-ethoxyimino)butyl]-3-hydroxycyclohex-2-en-1-one.

11. A compound according to claim 10, said compound being
5-(3-acetyl-2,4,6-trimethylphenyl)-2-[1-(ethoxyimino)propyl]-3-hydroxycyclohex-2-en-1-one.

12. A herbicidal composition comprising as active ingredient a herbicidal effective amount of a compound as defined according to claim 1 and a carrier therefor.

13. A process for severely damaging or killing unwanted plants which process comprises applying to said plant, or the growth medium of said plants, an effective amount of a compound as defined according to claim 1.

14. A process for selectively controlling the growth of monocotyledenous weeds in dicoytledonous crops which process comprises applying to said crop, or to the growth medium of said crop, a compound as defined according to claim 1 in an amount sufficient to severly damage or kill said weeds but insufficiently to substantially damage said crop.

15. A process according to claim 14 wherein the compound is applied at a rate in the range of from 0.005 to 20 kilograms per hectare.

* * * * *